United States Patent
Orr et al.

(10) Patent No.: US 9,005,981 B2
(45) Date of Patent: Apr. 14, 2015

(54) ASSAYS UTILIZING NICOTINIC ACETYLCHOLINE RECEPTOR SUBUNITS

(75) Inventors: Nailah Orr, Carmel, IN (US); Gerald B. Watson, Zionsville, IN (US); Gary D. Gustafson, Zionsville, IN (US); James M. Hasler, Danville, IN (US); Chaoxian Geng, Westford, MA (US); Scott Chouinard, Medford, MA (US); Kevin R. Cook, Bloomington, IN (US); Vincent L. Salgado, Durham, NC (US)

(73) Assignee: Dow AgroSciences LLC, Indianapolis, IN (US)

( * ) Notice: Subject to any disclaimer, the term of this patent is extended or adjusted under 35 U.S.C. 154(b) by 783 days.

(21) Appl. No.: 12/644,683

(22) Filed: Dec. 22, 2009

(65) Prior Publication Data

US 2010/0212029 A1  Aug. 19, 2010

Related U.S. Application Data

(60) Provisional application No. 61/141,277, filed on Dec. 30, 2008.

(51) Int. Cl.
| A01K 67/00 | (2006.01) |
| G01N 1/00 | (2006.01) |
| G01N 33/48 | (2006.01) |
| G01N 33/50 | (2006.01) |
| C07K 16/28 | (2006.01) |

(52) U.S. Cl.
CPC ........... *C07K 16/286* (2013.01); *C12N 2503/00* (2013.01); *C12N 2510/00* (2013.01); *G01N 2333/43552* (2013.01); *G01N 2333/70571* (2013.01); *G01N 2500/02* (2013.01); *C07K 2317/34* (2013.01)

(58) Field of Classification Search
USPC ............... 436/63; 536/23.1; 800/3, 13, 18, 20
See application file for complete search history.

(56) References Cited

U.S. PATENT DOCUMENTS

| 5,801,232 A | 9/1998 | Elliott et al. |
| 6,100,046 A | 8/2000 | Elgoyhen et al. |
| 6,440,681 B1 | 8/2002 | Elliott et al. |
| 6,485,967 B1 | 11/2002 | Elliott et al. |
| 6,524,789 B1 | 2/2003 | Elliott et al. |

FOREIGN PATENT DOCUMENTS

| EP | 0 962 528 | 12/1999 |
| EP | 1 184 390 | 3/2002 |
| EP | 1 184 391 | 3/2002 |
| WO | WO0171042 A2 | 9/2001 |
| WO | WO2004064522 A2 | 8/2004 |
| WO | WO2004074245 A2 | 9/2004 |
| WO | WO 2006/091672 | * 8/2006 |

OTHER PUBLICATIONS

Perry et al, Insect Biochem. Mol. Biol. 37:184-188, 2007.*
Tang et al, Genesis 34: 39-45, 2002.*
Cook, K., Dec. 5, 2006, FlyBase Allele Report: Dmel/nAcRa3OD [DAS2].*
Parks et al, Nature Genetics 36(3):288-292, 2004.*
Salgado V. L. et al., "Desensitizing and non-desensitizing subtype of alpha-bungarotixin-sensitive nicotinic acetylcholine receptors in cockroach neurons," Journal of Insect Physiology, Pergamon Press, GB vol. 50, No. 10 Oct. 2004, pp. 867-879.
Halevi Sarah et al., "Conservation within the RIC-3 gene family, effectors of mammalian nicotinic acetylcholine receptor expression," Journal of Biological Chemistry Sep. 5, 2003, vol. 278, No. 36, pp. 34411-34417.
Halevi Sarah et al., "The C. elegans ric-3 gene is required for maturation of nicotinic acetylcholine receptors," The Embo Journal, Mar. 1, 2002, pp. 1012-1020.
Lansdell et al., "Molecular characterization of Da6 and Da7 nicotinic acetylcholine receptor subunits from Drospohila: formation of a high-affinity a-bungarotoxin binding site revealed by expression of subunit chimeras," Journal of Neurochemistry, 2004, pp. 479-489, vol. 90.
Grauso, et al., "Novel putative nicotinic acetylcholine receptor subunit genes, Da5, Da6, Da7, in *Drosophila melanogaster* Identify a new and highly conserved target of adenosine deaminase acting on RNA-mediated A-to-I pre-mRNA editing," Genetics Society of America, Apr. 2002, pp. 1419-1533, vol. 160.
International Search Report for PCT/US2006/006284, dated Mar. 1, 2007.
Written Opinion for PCT/US2006/006284, dated Mar. 1, 2007.
International Preliminary Report on Patentability for PCT/US2006/006284, dated Aug. 28, 2007.

* cited by examiner

*Primary Examiner* — Kevin Hill
(74) *Attorney, Agent, or Firm* — Eric J. Kraus; Traskbritt, P.C.

(57) ABSTRACT

The present invention is in the field of identification and characterization of novel insecticidal target sites and, in particular, relates to host cells, assays and antibodies thereto.

17 Claims, No Drawings

US 9,005,981 B2

ASSAYS UTILIZING NICOTINIC ACETYLCHOLINE RECEPTOR SUBUNITS

This application claims the benefit of U.S. Provisional Application No. 61/141,277, filed on Dec. 30, 2008.

GOVERNMENT INTERESTS

This invention was made with government support under Grant No. 5-U01-AI053873 awarded by the National Institutes of Health. The government has certain rights in the invention.

FIELD OF THE INVENTION

The present invention is in the field of identification and characterization of novel insecticidal target sites and, in particular, relates to host cells, assays and antibodies thereto.

BACKGROUND OF THE INVENTION

Global economic loss resulting from insect damage to crops is staggering. The economic loss due to damage caused just by Lepidopteran pests in the United States is estimated to be greater than 600 million dollars annually. Accordingly, insecticides are integral components of pest control for modern agriculture. One such insecticide, spinosad, is a mixture of two naturally-occurring metabolites, spinosyn A and spinosyn D, produced by the actinomycete *Saccharapolyspora spinosa*. Spinosad provides effective control of pests in the insect orders *Lepidoptera*, Diptera and Thysanoptera, and is also effective against some species of Coleoptera and Orthoptera.

Insecticides such as spinosad generally affect a specific target site, such as a critical protein, within an organism. To date, a limited number of insecticidal target sites have been identified, and many of the insecticides acting at these target sites are losing their effectiveness due to increased resistance in field populations of insects. While spinosad has been used as a naturally-occurring insect control agent, it would be desirable to identify other chemical compounds possessing insecticidal activity that act at the spinosad target site.

Despite various technological advances, the general state of understanding of insecticidal target sites is extremely limited and a need exists for the discovery and development of novel, efficacious and safe insecticides. The present invention addresses this need by providing a novel target site, i.e., the spinosad target site, which is useful for the identification and characterization of new chemistries acting in a manner similar to spinosad and its chemical constituents. In addition, nicotinic acetylcholine receptors from vertebrate species are important target sites for pharmaceutical and animal health compounds that intervene in a number of disease states. Therefore, the present invention also provides a model system for studying nicotinic acetylcholine receptor subunit interactions and pharmacology.

BRIEF DESCRIPTION OF THE SEQUENCE LISTINGS

SEQUENCE ID NO: 1 is a nucleotide sequence encoding a nicotinic acetylcholine receptor alpha-5 subunit located at position 34E on chromosome 2L of *Drosophila melanogaster*;

SEQUENCE ID NO: 2 is a nucleotide sequence encoding a nicotinic acetylcholine receptor alpha-7 subunit located at position 18C on chromosome X of *Drosophila melanogaster*;

SEQUENCE ID NO: 3 is a nucleotide sequence encoding a forward PCR primer for a *Drosophila* nicotinic acetylcholine alpha-6 receptor subunit located at 30D;

SEQUENCE ID NO: 4 is a nucleotide sequence encoding a reverse PCR primer for a *Drosophila* nicotinic acetylcholine alpha-6 receptor subunit located at 30D;

SEQUENCE ID NO: 5 is a nucleotide sequence encoding a forward PCR primer for a *Drosophila* nicotinic acetylcholine alpha-5 receptor subunit located at 34E;

SEQUENCE ID NO: 6 is a nucleotide sequence encoding a reverse PCR primer for a *Drosophila* nicotinic acetylcholine alpha-5 receptor subunit located at 34E;

SEQUENCE ID NO: 7 is a nucleotide sequence encoding a forward PCR primer for a *Drosophila* nicotinic acetylcholine alpha-7 receptor subunit located at 18C;

SEQUENCE ID NO: 8 is a nucleotide sequence encoding a reverse PCR primer for a *Drosophila* nicotinic acetylcholine alpha-7 receptor subunit located at 18C;

SEQUENCE ID NO: 9 is a nucleotide sequence encoding a forward PCR primer for *C. elegans* ric-3;

SEQUENCE ID NO: 10 is a nucleotide sequence encoding a reverse PCR primer for *C. elegans* ric-3;

SEQUENCE ID NO: 11 is an amino acid sequence corresponding to amino acids 367-380 of the *Drosophila* nicotinic acetylcholine alpha-6 receptor subunit;

SEQUENCE ID NO: 12 is a nucleotide sequence encoding a forward PCR primer for 30D nAChR alpha6 with an added Kozak translation initiation signal.

SEQUENCE ID NO: 13 is a nucleotide sequence encoding a reverse PCR primer for 30D nAChR alpha6.

SEQUENCE ID NO: 14 is a nucleotide sequence encoding a forward PCR primer for *C. elegans* ric3, with an added Kozak translation initiation signal.

SEQUENCE ID NO: 15 is a nucleotide sequence encoding alpha-6 subunit located at position 30D on chromosome 2L of *Drosophila melanogaster*.

The Sequence Listing contains the one letter code for nucleotide sequence characters and the one letter codes for amino acids as defined in conformity with the IUPAC-IUBMB standards described in Nucleic Acids Res. 13:3021-3030 (1985) and in the Biochemical J. 219 (No. 2):345-373 (1984) which are herein incorporated by reference. The symbols and format used for nucleotide and amino acid sequence data comply with the rules set forth in 37 C.F.R. §1.822.

SUMMARY OF THE INVENTION

One aspect of the present invention relates to a host cell comprising (i) a nucleic acid which has at least 50% identity to SEQ ID NO. 15 encoding a receptor subunit; and, (ii) a nucleic acid encoding an ion channel subunit, wherein the host cell is capable of responding to a spinosyn.

An additional aspect of the present invention relates to a host cell comprising (i) a nucleic acid which has at least 50% identity to SEQ ID NO. 15 encoding a receptor subunit; and, (ii) a nucleic acid encoding an accessory protein, wherein the host cell is capable of responding to a spinosyn.

A further aspect of the present invention relates to a method of assaying a chemical compound for ability to influence a receptor subunit, comprising the steps of: (a) introducing (i) a nucleic acid which has at least 50% identity to SEQ ID NO. 15 encoding a receptor subunit; and, (ii) a nucleic acid molecule encoding an ion channel subunit into a host cell in vitro to express the receptor subunit and the ion channel subunit, wherein the host cell is capable of responding to a spinosyn; (b) exposing the receptor subunit to a chemical compound;

and, (c) evaluating the exposed receptor subunit to determine if the chemical compound influences the receptor subunit.

Another aspect of the present invention relates to a method of assaying a chemical compound for ability to influence a receptor subunit, comprising the steps of: (a) introducing (i) a nucleic acid which has at least 50% identity to SEQ ID NO. 15 encoding a receptor subunit into a host cell in vitro to express the receptor subunit, wherein an ion channel subunit is endogenously produced and expressed by the host cell, wherein the host cell is capable of responding to a spinosyn; (b) exposing the expressed receptor subunit to a chemical compound; and, (c) evaluating the exposed receptor subunit to determine if the chemical compound influences the receptor subunit.

A further aspect of the present invention relates to a method of assaying a chemical compound for ability to influence a receptor subunit, comprising the steps of: (a) introducing (i) a nucleic acid which has at least 50% identity to SEQ ID NO. 15 encoding a receptor subunit; and, (ii) an isolated nucleic acid molecule encoding an accessory protein into a host cell in vitro to express the receptor subunit and the accessory protein, wherein the host cell is capable of responding to a spinosyn; (b) exposing the expressed receptor subunit to a chemical compound; and, (c) evaluating the exposed receptor subunit to determine if the chemical compound influences the receptor subunit.

Yet another aspect of the present invention relates to a method of assaying a chemical compound for ability to influence a receptor subunit, comprising the steps of: (a) a nucleic acid which has at least 50% identity to SEQ ID NO. 15 encoding a receptor subunit into a host cell in vitro to express the receptor subunit, wherein an accessory protein is endogenously produced and expressed by the host cell, wherein the host cell is capable of responding to a spinosyn; (b) exposing the expressed receptor subunit to a chemical compound; and, (c) evaluating the exposed receptor subunit to determine if the chemical compound influences the receptor subunit.

One further aspect of the present invention relates to an antibody that specifically binds to an epitope of a polypeptide encoded by a nucleic acid which has at least 50% identity to SEQ ID NO. 15, and wherein a host cell which functionally expresses the polypeptide encoded by the nucleic acid is capable of responding to a spinosyn.

Another aspect of the present invention relates to an organism comprising a mutation in a gene, wherein a coding region of the gene has at least 50% identity to SEQ ID NO. 15, and wherein the organism comprising the mutation exhibits a reduced response to a spinosyn relative to a parental organism from which the mutant is derived.

Yet even another aspect of the present invention is a vector comprising: (a) an antisense nucleotide sequence substantially complementary to (1) a corresponding portion of one strand of a DNA molecule which has at least 50% identity to SEQ ID NO. 15; and (b) regulatory sequences operatively linked to the antisense nucleotide sequence such that the antisense nucleotide sequence is expressed in a cell into which it is transformed, and wherein the transformed cell exhibits a reduced response to a spinosyn relative to an untransformed cell.

One more aspect of the present invention is a method of screening an organism for resistance to a spinosyn comprising the steps of: (a) obtaining nucleic acid from the organism; (b) determining the sequence of a nucleic acid which has at least 50% identity to SEQ ID NO. 15; and (c) comparing the determined sequence to a sequence from the same gene of a spinosyn susceptible organism, wherein the screened organism and the spinosyn susceptible organism are from the same species.

In a further embodiment, the present invention relates to a method of assaying a chemical compound for ability to influence a receptor subunit, comprising the steps of: (a) introducing a vector comprising: (i) a nucleotide sequence which has at least 50% identity to SEQ ID NO. 15; and (ii) regulatory sequences operatively linked to the nucleotide sequence, into one or more cells of an organism such that the nucleotide sequence is expressed in at least the one or more cells into which it is transformed, and wherein the transformed cell exhibits an increased response to a spinosyn relative to an untransformed cell; (b) exposing transformed cells expressing the receptor subunit to a chemical compound; and, (c) evaluating the exposed receptor subunit to determine if the chemical compound influences the receptor subunit.

Additional features and advantages of the invention will be set forth in the description that follows, and in part will be apparent from the description, or may be learned by practice of the invention. The advantages of the invention will be realized and attained by the inventions particularly pointed out in the written description and claims hereof. It is to be understood that both the foregoing general description and the following detailed description are exemplary and explanatory and are intended to provide further explanation of the invention as claimed.

DETAILED DESCRIPTION OF THE INVENTION

1. Definitions

Definitions are herein provided to facilitate understanding of the invention. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

"Accessory protein" refers to any protein involved in membrane trafficking, ion channel subunit maturation, folding, transport and/or assembly of a polypeptide such as a receptor subunit, including, but not limited to insect and invertebrate accessory proteins such as chaperone proteins. "Nucleic acid encoding an accessory protein" or "accessory protein polynucleotide" refers to a polynucleotide encoding an accessory protein. The term also includes fragments, variants, homologs, alleles or precursors (e.g., preproteins or proproteins) of any of the accessory proteins.

"Antibody" refers to intact molecules as well as fragments thereof that are capable of specific binding to an epitopic determinant Antibodies that bind a polypeptide (for example, a polypeptide encoded by a nucleic acid of the present invention) can be prepared using intact polypeptides or fragments as the immunizing antigen. These antigens may be conjugated to a carrier protein, if desired.

"Antisense RNA" refers to an RNA transcript that is complementary to all or part of a target primary transcript or mRNA and that blocks the expression of a target gene (U.S.

Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

"Binding affinity" refers to the propensity of a ligand to interact with a receptor or other protein.

"Ion transport" refers to the movement of salts and other electrolytes in the form of ions from place to place within living systems.

"Epitope" refers to any region of a macromolecule with the ability or potential to elicit, and combine with, one or more specific antibodies, including that portion of a molecule that makes contact with a particular antibody.

"Expression" refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Functional expression" refers to the synthesis and any necessary post-translational processing of an ion channel molecule in a host cell so that the channel is inserted properly in the cell membrane and is capable of ion transport in response to an experimentally-imposed change in the cell membrane potential or upon exposure to appropriate pharmacological compounds.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Genomic DNA" refers to chromosomal DNA and can include introns. An "intron" is an intervening sequence. It is a non-coding sequence of DNA within a gene that is transcribed into heterogenous nuclear RNA (hnRNA) but is then removed by RNA splicing in the nucleus, leaving a mature mRNA which is then translated in the cytoplasm. The regions at the ends of an intron are self-complementary, allowing a hairpin structure to form naturally in the hnRNA.

"Host cell" refers to any cell or organism into which an isolated nucleic acid fragment may be stably or transiently introduced. The host cell may be part of a larger organism, an individual in tissue culture, or a free-living organism. These include, but are not limited to, vertebrate and invertebrate hosts, eukaryotic hosts such as mammalian cells (i.e., SH-SY5Y cells, COS cells, HEK-293, PC12), rats and mice, well known model organisms such as zebrafish, *Xenopus* oocytes, insect cells (i.e. insect cell lines such as *Drosophila* Schneider, *Drosophila* $K_c$, Sf9, and High Five), prokaryotic hosts such as bacteria (including but not limited to strains of *E. coli, Bacillus, Streptomyces* and *Pseudomonas*), as well as fungi (including but not limited to cells from species of *Aspergillus* and *Trichoderma*), yeasts (including but not limited to cells from species of *Kluyveromyces* or *Saccharomyces*) and plants.

"Insect" includes any air-breathing arthropod of the class Insecta including, but not limited to *Musca domestica* (housefly), fruit or vinegar flies (*Drosophila melanogaster*), as well as any other insect of agricultural, medical or veterinary importance, such as *Myzus persicae* (green peach aphid), *Heliothis virescens* (tobacco budworm) *Leptinotarsa decemlineata* (Colorado potato beetle), *Blattella germanica* (German cockroach), codling moth, diamondback moth, *Aedes aegypti* and *Anopheles gambiae*.

"Ion channel subunit" refers to any proteinaceous molecule that forms part of an ion channel, including subunits that can combine with other molecules in the formation of an ion channel. "Nucleic acid encoding an ion channel subunit" or "ion channel subunit polynucleotide" refers to a polynucleotide encoding an ion channel subunit. The term also includes fragments, variants, homologs, alleles or precursors (e.g., preproteins or proproteins) of any of the ion channel subunits. The term "nucleic acid encoding an ion channel subunit" also encompasses embodiments where the nucleic acid is endogenously produced by a host cell such as PC12 cells.

"Isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

"Lesion" refers to any molecular alteration of a nucleic acid relative to the parental nucleic acid from which it was derived or to the nucleic acid obtained from a wild-type population. For instance, a lesion can be a deletion, inversion, insertion, duplication, transition, transversion or a rearrangement in a nucleic acid sequence.

"Ligand-gated ion channel subunit" refers to a subunit that forms part of any ion channel which can be regulated by a ligand. This includes, but is not limited to nicotinic acetylcholine receptor subunits, GABA receptor subunits, serotonin receptor subunits and glutamate receptor subunits. Nucleic acid sequences, protein sequences, as well as multiple sequence alignments and phylogenetic studies are known and available from public databases and via the worldwide web. "Nucleic acid encoding a ligand-gated ion channel subunit" or "ligand-gated ion channel subunit polynucleotide" refers to a polynucleotide encoding a ligand-gated ion channel subunit. The term also includes fragments, variants, homologs, alleles or precursors (e.g., preproteins or proproteins) of any of the ligand-gated ion channel subunits.

"Nucleic acid" refers to any nucleic acid and includes single or multi-stranded polymers of deoxyribonucleotide or ribonucleotide bases. Nucleic acids may also include fragments, modified nucleotides and variants. Therefore, as used herein, the terms "polynucleotide" and "nucleic acid" are used interchangeably.

"Promoter" typically refers to a DNA sequence which directs the transcription of a structural gene to produce RNA. Typically, a promoter is located in the region 500 base pairs upstream of a gene, proximal to the transcription start site. If a promoter is an inducible promoter, then the rate of transcription increases or decreases in response to an exogenous or endogenous inducing agent. In contrast, the rate of transcription is not regulated by an inducing agent if the promoter is a constitutive promoter.

"Receptor subunit" refers to any protein that is a constituent of an intact receptor. "Nicotinic acetylcholine receptor subunit" refers to any protein that is a constituent of an intact nicotinic acetylcholine receptor, e.g., nicotinic acetylcholine alpha-5, alpha-6 and alpha-7 receptor subunits. All references to nucleic acids encoding the aforementioned receptor subunits refer to a polynucleotide encoding the receptor subunit. The terms also include fragments, variants, homologs, alleles or precursors (e.g., preproteins or proproteins) of any of the receptor subunits.

"Resistance" refers to the relative responses of genetically-defined insect populations to the effects of a spinosyn. In general, an insect strain or population is considered "resistant" if it exhibits tolerance to a test insecticide (assessed as the dose required to poison 50% of a treated population or group) that is at least 2 times greater, preferably 4-8 times greater, and most preferably at least 10 times greater than the tolerance of an appropriate reference, or "susceptible" population.

"Responding to a spinosyn" refers to a measurable effect resulting from exposure to a spinosyn including, but not limited to alterations in behavior, viability, ligand binding or ion transport.

"Spinosyn" refers to fermentation products including those identified in U.S. Pat. No. 5,362,634 as A83543 which are produced by Saccharopolyspora spinosa. These compounds have been referred to as factors or components A, B, C, D, E, F, G, H, J, K, L, M, N, O, P, Q, R, S, T, U, V, W, Y, and the like (also see published international patent application WO 93/09126 and WO 94/20518) and are hereinafter referred to as spinosyn A, B, C, and so on. The naturally produced spinosyn compounds consist of a 5,6,5-tricylic ring system, fused to a 12-membered macrocyclic lactone, a neutral sugar (rhamnose), and an amino sugar (forosamine) (see Kirst et al., 1991). These and other natural spinosyn compounds including 21-butenyl spinosyn produced by Saccharopolyspora pagona may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyn compounds are also disclosed in U.S. Pat. Nos. 5,496,931, 5,670,364, 5,591,606, 5,571,901, 5,202,242, 5,767,253, 5,840,861, 5,670,486 and 5,631,155. Spinosyn A and spinosyn D are two spinosyns that are particularly active insecticides. A product comprised mainly of these two spinosyns (approximately 85% spinosyn A and approximately 15% spinosyn D) is produced by Dow AgroSciences (Indianapolis, Ind.) known as spinosad. As used herein, the term spinosyn also includes "spinosyn derivatives" which are synthetic or semi-synthetic spinosyns.

"Substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of nucleic acid fragments such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished by using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not affect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences encoded by the nucleic acid sequences reported herein. More preferred nucleic acid fragments encode amino acid sequences that are 90% similar to the amino acid sequences encoded by the nucleic acid sequences reported herein. Most preferred are nucleic acid fragments that encode amino acid sequences that are 95% similar to the amino acid sequences encoded by the nucleic acid sequences reported herein. Sequence alignments and percent similarity calculations were performed using programs from the Vactor NTi Suite (InforMax, North Bethesda, Md.). Multiple alignments of the sequences were performed using the Clustal method of alignment (Higgins and Sharp, 1989) with the default parameters (GAP PENALTY=10, GAP extension PENALTY=0.1) (hereafter, Clustal algorithm). Default parameters for pairwise alignments using the Clustal method were KTUPLE 1, GAP PENALTY=3, WINDOW=5 and DIAGONALS SAVED=5.

A "substantial portion" of an amino acid or nucleotide sequence refers to enough of the amino acid sequence of a polypeptide or the nucleotide sequence of a gene to afford putative identification of that polypeptide or gene, either by manual evaluation of the sequence by one skilled in the art, or by computer automated sequence comparison and identification using algorithms such as BLAST (Basic Local Alignment Search Tool; Altschul et al., 1993;). In general, a sequence of ten or more contiguous amino acids or thirty or more nucleotides is necessary to putatively identify a polypeptide or nucleic acid sequence as homologous to a known protein or gene. Moreover, with respect to nucleotide sequences, gene specific oligonucleotide probes comprising 20 30 contiguous nucleotides may be used in sequence dependent methods of gene identification (e.g., Southern hybridization) and isolation (e.g., in situ hybridization of bacterial colonies or bacteriophage plaques). In addition, short oligonucleotides of 12 15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art.

"Transcription regulatory region" and "regulatory region" refer to the section of DNA which regulates gene transcription. A regulatory region may include a variety of cis-acting elements, including, but not limited to, promoters, enhancers and hormone response elements. Also, since introns and 5' UTR have been known to influence transcription, a transcription regulatory region can include such sequences. A regulatory region may be operatively linked to a nucleic acid to ensure expression of the nucleic acid in a host cell.

"Transgenic animal" refers to an animal that has been modified by the artificial insertion, and stable integration, of DNA into its genome. The DNA may be inserted randomly or targeted to a specific site in a chromosome or an episomal or extrachromosomal element.

"Transgenic cell" refers to a cell containing artificially inserted DNA within a chromosome or an episomal or extrachromosomal element.

"Variant" refers to substantially similar sequences. Generally, nucleic acid sequence variants of the invention will have at least 46%, 48%, 50%, 52%, 53%, 55%, 60%, 65%, 70%, 75%, 76%, 77%, 78%, 79%, 80%, 85%, 86%, 87%, 88%, 89%, 90%, 91%, 92%, 93%, 94%, 95%, 96%, 97%, 98% or 99% sequence identity to the native nucleotide sequence, wherein the % sequence identity is based on the entire sequence and is determined by GAP 10 analysis using default parameters. Generally, polypeptide sequence variants of the invention will have at least about 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to the native protein, wherein the % sequence identity is based on the entire sequence and is determined by GAP 10 analysis using default parameters. GAP uses the algorithm of Needleman and Wunsch (J. Mol. Biol. 48:443-453, 1970) to find the alignment of two complete sequences that maximizes the number of matches and minimizes the number of gaps.

"Variant" also refers to substantially similar sequences that contain amino acid sequences highly similar to the motifs contained within the invention and optionally required for the biological function of the invention. Generally, polypeptide sequence variants of the invention will have at least 85%, 90% or 95% sequence identity to the conserved amino acid residues in the defined motifs.

Standard recombinant DNA and molecular cloning techniques used herein are well known in the art and are described more fully in Sambrook and Russell (2000).

Variants included in the invention may contain individual substitutions, deletions or additions to the nucleic acid or polypeptide sequences which alter, add or delete a single amino acid or a small percentage of amino acids in the encoded sequence. A "conservatively modified variant" is an alteration which results in the substitution of an amino acid with a chemically similar amino acid. When the nucleic acid is prepared or altered synthetically, advantage can be taken of known codon preferences of the intended host.

The nucleic acid fragments of the instant invention may be used to isolate cDNAs and genes encoding homologous proteins from the same or other species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other nicotinic acetylcholine receptor alpha-6 subunits, either as cDNAs or genomic DNAs, could be isolated directly by using all or a portion of the instant nucleic acid fragments as DNA hybridization probes to screen libraries from any desired organism employing methodology well known to those skilled in the art. Specific oligonucleotide probes based upon the instant nucleic acid sequences can be designed and synthesized by methods known in the art (Sambrook and Russell, 2000). Moreover, the entire sequences can be used directly to synthesize DNA probes by methods known to the skilled artisan such as random primer DNA labeling, nick translation, or end-labeling techniques, or RNA probes using available in vitro transcription systems.

In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding genes. Alternatively, the second primer sequence may be based upon sequences derived from the cloning vector. For example, the skilled artisan can follow the RACE protocol (Frohman et al., 1988) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (Invitrogen, Madison, Wis.), specific 3' or 5' cDNA fragments can be isolated (Ohara et al., 1989; Loh et al., 1989). Products generated by the 3' and 5' RACE procedures can be combined to generate full-length cDNAs (Frohman and Martin, 1989). Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, 1984; Sambrook and Russell, 2000).

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene. A variant may also be described as, for example, a "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotides that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base.

Variants of nucleic acids included in the invention can be obtained, for example, by oligonucleotide-directed mutagenesis, linker-scanning mutagenesis, mutagenesis using the polymerase chain reaction, and the like. Also, see generally, McPherson (1991). Thus, the present invention also encompasses DNA molecules comprising nucleotide sequences that have substantial sequence similarity with the inventive sequences.

With respect to particular nucleic acid sequences, "conservatively modified variants" refer to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the claimed invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of, from 1 to 50 can be so altered. Thus, for example, 1, 2, 3, 14, 25, 37, 45 or 50 alterations can be made. Conservatively modified variants typically provide similar biological activity as the unmodified polypeptide sequence from which they are derived. For example, substrate specificity, enzyme activity, or ligand/receptor binding is generally at least 20%, 30%, 40%, 50%, 60%, 70%, 80%, or 90% of the native protein for its native substrate. Conservative substitution tables providing functionally similar amino acids are well known in the art.

For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). Other acceptable conservative substitution patterns known in the art may also be used, (see Creighton, 1984); such as the scoring matrices of sequence comparison programs like the GCG package, BLAST, or CLUSTAL for example.

"Vector" refers to a nucleic acid molecule capable of transporting another nucleic acid to which it has been linked One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"Voltage-gated ion channel subunit" refers to a subunit that forms part of any ion channel which is regulated by changes in voltage. These include, but are not limited to calcium, sodium, potassium and chloride voltage-gated ion channel subunits. Nucleic acid sequences encoding such voltage-gated ion channels are known and available publicly from the NCBI database. "Nucleic acid encoding a voltage-gated ion channel subunit" or "voltage-gated ion channel subunit polynucleotide" refers to a polynucleotide encoding a voltage-gated ion channel subunit. The term also includes fragments, variants, homologs, alleles or precursors (e.g., preproteins or proproteins) of any of the voltage-gated ion channel subunits.

2. Detailed Description

Embodiments of the present invention relate to host cells that contain particular nucleic acids and are capable of expressing, under suitable conditions, certain amino acids. The host cells of the invention comprise a nucleic acid which presents at least 50% identity, preferably at least 60% identity, particularly at least 70% identity, more preferably at least 80% identity and especially 90%, 91%, 92%, 93%, 94%, 95%, 96%, 97%, 98%, 99% and 100% identity with SEQ ID NO. 15 encoding a receptor subunit, preferably over a length of at least 100, particularly over at least 500, contiguous nucleotides and especially over the entire length of the sequence. The gene having SEQ ID NO. 15 is located at position 30D on chromosome 2L of the *Drosophila melanogaster* genome. Exemplary nucleic acid sequences include, but are not limited to nucleic acid sequences of *Drosophila* and other invertebrates, e.g., *Caenorhabditis elegans* (NCBI Accession No. NM 072806), *Anopheles gambiae* (NCBI Accession No. AY705401), *Aphis mellifera* (NCBI Accession No. AY 500239), and *Heliothis virescens* (NCBI Accession No. AF143847). The amino acid sequences corresponding to these exemplary nucleic acid sequences are also publicly known and available.

In some embodiments, this nucleic acid sequence encodes a nicotinic acetylcholine receptor alpha-6 subunit. In other embodiments, the nucleic acid sequence encoding the receptor subunit is a nucleic acid comprising a sequence selected from the group consisting of: (a) a nucleic acid sequence having SEQ ID NO. 15; (b) sequences that encode a splice variant of the receptor subunit from *Drosophila melanogaster* having SEQ ID NO 15, including, e.g., those that are known and available from public databases (NCBI Accession Nos. NM 164874, NM 205951, NM 135472, NM 205952, NM 205953 AF321445, AF321446, AF321447, AF321448, NM 205953 and AF321449); and, (c) sequences which, owing to degeneracy of the genetic code, encode the same amino acid sequence as the sequences defined in (a)-(b).

In additional embodiments of the present invention, the host cells further comprise a nucleic acid encoding an ion channel subunit. It will be appreciated by those skilled in the art that the nucleic acid encoding the ion channel subunit may or may not be endogenously produced by the host cell. In the event that an ion channel subunit is endogenously produced, no need exists to separately introduce the nucleic acid into the host cells. Exemplary ion channel subunits include ligand-gated ion channel subunits such as nicotinic acetylcholine receptor subunits, gamma aminobutyric acid (GABA) receptor subunits, serotonin receptor subunits, glutamate receptor subunits, and functional fragments thereof, as well as voltage-gated ion channel subunits such as calcium, sodium, potassium, chloride voltage-gated ion channel subunits, and functional fragments thereof. In some embodiments the host cell comprises a nucleic acid encoding an ion channel subunit which is a nicotinic acetylcholine receptor subunit. In additional embodiments, the nucleic acid encoding the nicotinic acetylcholine receptor subunit comprises a sequence selected from the group consisting of (a) a nucleic acid sequence having SEQ ID No: 1 (b) a nucleic acid which has at least 50% identity, preferably at least 60% identity, particularly at least 70% identity, more preferably at least 80% identity and especially 90%, 91%, 92%, 93%, 94%, 95%, 96%, 97%, 98%, 99% and 100% identity with a sequence between position 925 and position 2424 of a coding region of a gene having SEQ ID No: 1, encoding a nicotinic acetylcholine receptor subunit, preferably over a length of at least 100, particularly over at least 500, contiguous nucleotides and especially over the entire length of the sequence; (c) sequences of nucleotides that encode a splice variant of the nicotinic acetylcholine receptor subunit including those that are known and available from public databases (NCBI Accession Nos. NM 176035, NM 205986, NM 205985, AF 272778); and, (d) sequences which, owing to degeneracy of the genetic code, encode the same amino acid sequence as the sequences defined in (a)-(c).

Mention should be made that the gene having SEQ ID No: 1 is located at position 34E on chromosome 2L of the *Drosophila melanogaster* genome.

In embodiments of the present invention, the host cell is capable of responding to a spinosyn. This can be determined by methods readily available and understood by those having ordinary skill in the art such as by, e.g., voltage-clamp analysis, ion flux assays gel-shift assays, Western blots, radiolabeled competition assay, phage-based expression cloning, and co-fractionation by chromatography as described herein.

In addition to host cells which comprise the above-referenced sequences, embodiments of the present invention also relate to host cells that further comprise a nucleic acid encoding an accessory protein. In particular embodiments, the nucleic acid encoding the accessory protein is a nucleic acid encoding an invertebrate accessory protein. In further embodiments, the nucleic acid encoding the accessory protein is a nucleic acid selected from the group consisting of a nucleic acid having NCBI Accession No NM 068898; (b) sequences which have at least 36% identity, preferably at least 40%, particularly at least 50%, preferably at least 60% identity, particularly at least 70% identity, more preferably at least 80% identity and especially 90%, 91%, 92%, 93%, 94%, 95%, 96%, 97%, 98%, 99% and 100% identity with a sequence between position 1 and position 1137 of a coding region of a gene having NCBI Accession No. NM 068898 encoding an accessory protein, preferably over a length of at least 100, particularly over at least 500, contiguous nucleotides and especially over the entire length of the sequence; (c) sequences which encode splice variants of the *Caenorhabditis elegans* ric-3 accessory protein having NCBI Accession No. NM 068898 and, (d) sequences which, owing to the degeneracy of the genetic code, encode the same amino acid sequence as the sequences defined in (a)-(c). Moreover, embodiments of the present invention also relate to host cells that may further comprise a second nucleic acid encoding an ion channel subunit. A particular second nucleic acid encoding an ion channel subunit is a second nucleic acid encoding a ligand-gated ion channel. In some embodiments, the host cell comprises a second nucleic acid encoding a ligand-gated ion channel subunit which is a nicotinic acetylcholine receptor subunit. In even other embodiments, the nucleic acid encoding the nicotinic acetylcholine receptor subunit a nucleic acid encoding a nicotinic alpha-7 receptor subunit. In yet further embodiments, the second nucleic acid encoding the nicotinic alpha-7 receptor subunit is a nucleic acid comprising a sequence selected from the group consisting of: (a) a nucleic acid which has at least 50% identity, preferably at least 60% identity, particularly at least 70% identity, more preferably at least 80% identity and especially 90%, 91%, 92%, 93%, 94%, 95%, 96%, 97%, 98%, 99% and 100% identity with a sequence between position 106 and position 1617 of a coding region of a gene having SEQ ID No: 2 encoding a nicotinic alpha-7 receptor subunit, preferably over a length of at least 100, particularly over at least 500, contiguous nucleotides and especially over the entire length of the sequence; (b) sequences which have at least 50% identity to the sequence encoding the nicotinic alpha-7 receptor subunit having SEQ ID No: 2 (c) splice variants of the sequence encoding the nicotinic alpha-7 receptor subunit from *Drosophila melanogaster*, including those that are known and available from public databases (NCBI Accession Nos. NM 206791, NM 167645, NM 206790, NM 080340, AJ 554210, AY 036614) and, (d) sequences which, owing to degeneracy of the genetic code, encode the same amino acid sequence as the sequences defined in (a)-(c). Mention should be made that the gene having SEQ ID No: 2 is located at position 18C on chromosome X of the *Drosophila melanogaster* genome.

Further embodiments of the present invention relate to a host cell comprising a nucleic acid which has at least 50% identity to SEQ ID NO. 15 encoding a receptor subunit; and, (ii) a nucleic acid encoding an accessory protein, wherein the host cell is capable of responding to a spinosyn. In these particular embodiments, a nucleic acid encoding an ion channel subunit need not be introduced into the host cell.

Another aspect of the present invention relates to host cells comprising vectors containing the aforementioned nucleic acid sequences, and preferably expression vectors. In embodiments of the present invention, vectors of the aforementioned type are provided, where the nucleotide sequence is operatively linked to and under the control of regulatory nucleotide sequences which are likewise present in the vector and which are arranged within the nucleotide sequence. These regulatory nucleotide sequences may be heterologous to the nucleotide sequence of the invention, i.e., they may be derived from a different organism or from a different gene, or homologous, i.e., naturally occurring together with the nucleotide sequences of the invention in a regulatory unit.

The recombinant expression vectors of the invention comprise a nucleic acid in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like.

The recombinant expression vectors can be designed for expression of the proteins in prokaryotic or eukaryotic cells. For example, the proteins can be expressed in bacterial cells such as *Escherichia coli*, insect cells (using baculovirus expression vectors) yeast cells or mammalian cells. Suitable host cells are discussed further in (Goeddel, 1990).

Having identified the host cells of the invention, the invention further provides methods of assaying a chemical compound for the ability of the chemical agent to interact with or to influence a receptor subunit, i.e., to act spinosyn-like. Thus, another aspect of the present invention relates to a method of assaying a chemical compound for ability to influence a receptor subunit, comprising the steps of: (a) introducing (i) a nucleic acid which has SEQ ID NO. 15 encoding a receptor subunit; and (ii) a nucleic acid molecule encoding an ion channel subunit into a host cell in vitro to express the receptor subunit and the ion channel subunit, wherein the host cell is capable of responding to a spinosyn; (b) exposing an expressed receptor subunit to a chemical compound; and, (c) evaluating the expressed and exposed receptor subunit to determine if the chemical compound influences the receptor subunit.

Various methods are known in the art for introducing nucleic acids into host cells. One method is microinjection, in which DNA is injected directly into the nucleus of cells through fine glass needles (or RNA is injected directly into the cytoplasm of cells). Alternatively, DNA can be incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. Some of the DNA evades destruction in the cytoplasm of the cell and escapes to the nucleus, where it can be transcribed into RNA like any other gene in the cell. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). DNA can also be incorporated into artificial lipid vesicles, liposomes, which fuse with the cell membrane, delivering their contents directly into the cytoplasm. In an even more direct approach, used primarily with plant cells and tissues, DNA is absorbed to the surface of tungsten microprojectiles and fired into cells with a device resembling a shotgun.

Several of these methods, microinjection, electroporation, and liposome fusion, have been adapted to introduce proteins into cells. For review, see Mannino and Gould-Fogerite, 1988; Shigekawa and Dower, 1988; Capecchi; 1980 and Klein et al., 1987.

Further methods for introducing nucleic acids into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces a crystal protein which encloses multiple virions (polyhedrin protein) to spectacular levels. If a foreign gene were to be substituted for this viral gene, it too ought to be produced at high level. Baculovirus, like Vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack polyhedrin crystals. The plaques with recombinant virus are picked and expanded. This virus stock is then used to infect a fresh culture of insect cells, resulting in high expression of the foreign protein. For a review of baculovirus vectors, see Miller (1989). Various viral vectors have also been used to transform mammalian cells, such as bacteriophage, vaccinia virus, adenovirus, and retrovirus.

As indicated, some of these methods of transforming a cell require the use of an intermediate plasmid vector. U.S. Pat. No. 4,237,224 to Cohen and Boyer describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture. The DNA sequences are cloned into the plasmid vector using standard cloning procedures known in the art, as described by Sambrook and Russell (2000).

In some embodiments of the present invention, host cells are utilized which endogenously produce a nucleic acid encoding an ion channel subunit and, accordingly, it is unnecessary to separately introduce nucleic acid encoding the ion channel subunit into the host cell. Thus, these embodiments relate to a method of assaying a chemical compound for ability to influence a receptor subunit, comprising the steps of: (a) introducing (i) the nucleic acid sequence encoding the receptor subunit into a host cell in vitro to express the receptor subunit, wherein an ion channel subunit is endogenously produced and expressed by the host cell, and wherein the host cell is capable of responding to a spinosyn; and thereafter, (b) exposing the receptor subunit to a chemical compound; and, (c) evaluating the exposed receptor subunit to determine if the chemical compound influences the receptor subunit.

Another aspect of the present invention relates to a method of assaying a chemical compound for ability to influence a receptor subunit, comprising the steps of: (a) introducing (i) a nucleic acid which has at least 50% identity to a nucleic acid sequence between position 79 and position 1485 of a coding region of a gene having SEQ ID NO. 15 encoding a receptor subunit; and (ii) a nucleic acid molecule encoding an accessory protein into a host cell in vitro to express the receptor subunit and the accessory protein, wherein the host cell is capable of responding to a spinosyn; (b) exposing the expressed receptor subunit to a chemical compound; and, (c) evaluating the expressed and exposed receptor subunit to determine if the chemical compound influences the receptor subunit.

In some embodiments of the present invention, host cells are utilized which endogenously produce an accessory protein and, accordingly, it is unnecessary to separately introduce nucleic acid encoding the accessory protein into the host cell. Thus, these embodiments relate to a method of assaying a chemical compound for ability to influence a receptor subunit, comprising the steps of: (a) introducing (i) the nucleic acid sequence encoding the receptor subunit into a host cell in vitro to express the receptor subunit, wherein an accessory protein is endogenously produced and expressed by the host cell, and wherein the host cell is capable of responding to a spinosyn; and thereafter, (b) exposing the expressed receptor subunit to a chemical compound; and, (c) evaluating the exposed receptor subunit to determine if the chemical compound influences the receptor subunit.

In any event, the host cells according to the present invention can be exposed to various chemical compounds such as potential insecticides and pesticides and evaluated for their interaction with these compounds to develop and identify new insect control compounds. In embodiments of the present invention, the chemical compound is a mixture of chemical compounds. Exemplary methods of screening are described in Eldefrawi et al. (1987) and Rauh et al. (1990).

The evaluation of the exposed host cell to determine if the chemical compound influences the receptor subunit can be by any means known in the art. In one embodiment, the evaluation comprises monitoring ion transport, e.g., through an ion channel, such as by voltage-clamp analysis of the ion channel following the functional expression of the channel in oocytes of the frog Xenopus laevis (see Taglialatela et al., 1992 and Stuhmer, 1992, for a general discussion of the voltage-clamp analysis of receptors and ion channels expressed in Xenopus oocytes).

Ion transport can be monitored by pre-incubating cells in a medium containing one or more chemical compounds, adding a medium containing a radiotracer such as radiocalcium ($^{45}Ca^{2+}$) or radiosodium ($^{22}Na^+$), incubating the cells further in this medium, and isolating cells by filtration. Ion transport is detected by the measurement of the radiotracer within the cells by liquid scintillation counting or other radiometric techniques (Bloomquist and Soderlund, 1988). In another embodiment, the influence of the chemical compound on the receptor can be evaluated by pre-incubating cells to equilibrium with a calcium- or sodium-selective fluorescent chelating agent, washing the cells, exposing the cells to a test agent, and monitoring the increase in intracellular calcium or sodium by measuring the fluorescence. (Deri and Adam-Vizi, 1993; Lin, et al., 1999; PCT Int. Appl. WO 2004033647; PCT Application: WO 20031009; Wilcox, 1999).

In a further embodiment, the influence of the chemical compound on the receptor subunit can be evaluated by measuring binding affinity of the compound to the receptor subunit. Binding can be determined by binding assays which are well known to the skilled artisan, including, but not limited to, gel-shift assays, Western blots, radiolabeled competition assay, phage-based expression cloning, co-fractionation by chromatography, co-precipitation, cross linking, interaction trap/two-hybrid analysis, Southwestern analysis, ELISA, and the like, which are described in, for example, Current Protocols in Molecular Biology (1999, John Wiley & Sons, NY), which is incorporated herein by reference in its entirety. The compounds to be screened include any compounds and are not limited to, extracellular, intracellular, biologic or chemical origin. The methods of the invention also embrace ligands, especially potential pesticides, that are attached to a label, such as a radiolabel, a fluorescence label, a chemiluminecent label, an enzymatic label and an immunogenic label. The nucleic acids employed in such a test may either be free in solution, attached to a solid support, borne on a cell surface or located intracellularly or associated with a portion of a cell. One skilled in the art can, for example, measure the formation of complexes between receptor subunits and the compound being tested. Alternatively, one skilled in the art can examine the diminution in complex formation between receptor subunits and its substrate caused by the compound being tested.

Additionally, the present assays are particularly suited to the development of high-throughput screens where detection may be carried out using for example a CCD camera, a luminometer, or any other suitable light detection system. In this manner, cells may be provided for example in multi-well plates to which test substances and reagents necessary for the detection of intracellular calcium may be added. Moreover, commercially available instruments such as "FLIPR-fluorimetric imaging based plate reader" (Molecular Devices Corp, Sunnyvale, Calif., USA; Wood et al., 2000) and "VIPR" voltage ion probe reader (Aurora, Bioscience Corp. CA, USA) may be used. Very precise measurement of cellular fluorescence in a high throughput whole cell assay has become possible with the "FLIPR." FLIPR has shown considerable utility in measuring membrane potential of mammalian cells using voltage-sensitive fluorescent dyes but is useful for measuring essentially any cellular fluorescence phenomenon. The device uses low angle laser scanning illumination and a mask to selectively excite fluorescence within approximately 200 microns of the bottoms of the wells in standard 96 well plates. The low angle of the laser reduces background by selectively directing the light to the cell monolayer. This avoids background fluorescence of the surrounding media. This system then uses a CCD camera to image the whole area of the plate bottom to measure the resulting fluorescence at the bottom of each well. The signal measured is averaged over the area of the well and thus measures the average response of a population of cells. The system has the advantage of measuring the fluorescence in each well simultaneously thus avoiding the imprecision of sequential measurement well by well measurement. The system is also designed to read the fluorescent signal from each well of a 96 or 384 well plate as fast as twice a second. This feature provides FLIPR with the capability of making very fast measurements in parallel. This property allows for the measurement of changes in many physiological properties of cells that can be used as surrogated markers to a set of functional assays for drug discovery. FLIPR is also designed to have state of the art sensitivity. This allows it to measure very small changes with great precision. New fluorescent indicators for calcium called "chameleons" may also be used and are genetically encoded without cofactors and are targetable to specific intracellular locations. These so-called "chameleons" consist of tandem fusions of a blue- or cyan-emitting mutant of the green fluorescent protein (GFP), calmodulin, the calmodulin-binding peptide M13, and an enhanced green- or yellow-emitting GFP. Binding of calcium makes calmodulin wrap around to M13 domain, increasing (Miyawaki et al., 1997) or decreasing (Romoser et al., 1997) the fluorescence resonance energy transfer between flanking GFPs.

Having identified various host cells and methodologies of the present invention, further provided are antibodies which can be raised to, i.e., which specifically bind to an epitope of a polypeptide encoded by a nucleic acid which has at least 50% identity, preferably at least 60% identity, particularly at least 70% identity, more preferably at least 80% identity and especially 90%, 91%, 92%, 93%, 94%, 95%, 96%, 97%, 98%, 99% and 100% identity to SEQ ID NO. 15, and wherein a host cell which expresses, preferably functionally expresses, the polypeptide encoded by the nucleic acid is capable of responding to a spinosyn. Preferably, the antibody specifically binds to an epitope which is from amino acid 367 to amino acid 380 and the nucleic acid sequence is the nucleic acid sequence having SEQ ID NO. 15. Antibodies of the subject invention include polyclonal antibodies and monoclonal antibodies capable of binding to the identified epitope, as well as fragments of these antibodies, and humanized forms. Humanized forms of the antibodies of the subject invention may be generated using one of the procedures known in the art such as chimerization. Fragments of the antibodies of the present invention include, but are not limited to, the Fab, the Fab2, and the Fd fragments.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well known in the art (see Campbell, 1984 and St. Groth et al., 1980). Any animal (mouse, rabbit, etc.) which is known to produce antibodies can be immunized with the antigenic nicotinic acetylcholine receptor alpha-6 subunit protein (or an antigenic fragment thereof). Methods for immunization are well known in the art. Such methods include subcutaneous or intraperitoneal injection of the protein. One skilled in the art will recognize that the amount of the nicotinic acetylcholine receptor alpha-6 subunit protein used for immunization will vary based on the animal which is immunized, the antigenicity of the protein, and the site of injection.

The protein which is used as an immunogen may be modified or administered in an adjuvant to increase the protein's antigenicity. Methods of increasing the antigenicity of a protein are well known in the art and include, but are not limited to, coupling the antigen with a heterologous protein (such as a globulin or beta-galactosidase) or through the inclusion of an adjuvant during immunization. For monoclonal antibodies, spleen cells from the immunized animals are removed, fused with myeloma cells, such as SP2/O—Ag 15 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, Western blot analysis, or radioimmunoassay (Lutz et al., 1988). Hybridomas secreting the desired antibodies are cloned and the class and subclass are determined using procedures known in the art (Campbell, 1984). For polyclonal antibodies, antibody containing antisera is isolated from the immunized animal and is screened for the presence of antibodies with the desired specificity using one of the above-described procedures.

The present invention further provides the above-described antibodies in detectably labeled form. Antibodies can be detectably labeled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, nanoparticles, etc. Procedures for accomplishing such labeling are well known in the art, for example see Sternberger et al., 1970; Bayer et al., 1979; Engval et al., 1972; and Goding 1976; Ye et al., 2005).

The labeled antibodies or fragments thereof of the present invention can be used for in vitro, in vivo, and in situ assays to identify cells or tissues which express a receptor subunit with the identified epitope, to identify samples containing the receptor subunit proteins with the identified epitope, or to detect the presence of a receptor subunit with the identified epitope in a sample. More particularly, the antibodies or fragments thereof can thus be used to detect the presence of a receptor subunit with the identified epitope in a sample, by contacting the sample with the antibody or fragment thereof. The antibody or fragment thereof binds to any receptor subunit having the required epitope present in the sample, forming a complex therewith. The complex can then be detected, thereby detecting the presence of the receptor subunit in the sample.

Another aspect of the present invention relates to an organism comprising a gene, wherein a coding region of the gene has at least 50% identity to SEQ ID NO. 15 and wherein the organism comprising a mutation exhibits a reduced response to a spinosyn relative to a parental organism from which the mutant is derived.

Mutations in the gene of interest can result in organisms in which the receptor subunit protein is not expressed or, where the receptor subunit protein is expressed but contains an altered ligand binding site. Mutations in a gene can be generated by any of several mutagenesis methods known in the art (Ashburner, 1989; Wood, 1988). Techniques for producing mutations in a gene or genome include use of radiation (e.g., X-ray, UV, or gamma ray); chemicals (e.g., EMS, MMS, ENU, formaldehyde, etc.); and insertional mutagenesis by mobile elements including dysgenesis induced by transposon insertions, or transposon-mediated deletions, for example, male recombination, as described below. Other methods of altering expression of genes include use of transposons (e.g., P-element, EP-type "overexpression trap" element, mariner element, piggyBac transposon, hermes, minos, sleeping beauty, etc.) to misexpress genes; antisense; double-stranded RNA interference; peptide and RNA aptamers;

directed deletions; homologous recombination; dominant negative alleles; and intrabodies.

Mutagenesis can be achieved by a variety of mutagenic agents. Examples of mutagenic agents known in the art include, but are not limited to, chemical mutagens (e.g., DNA-intercalating or DNA-binding chemicals which affect (e.g., increase or decrease) the activity, protein coding potential or expression of a gene contained on a DNA molecule to which the chemical has bound), physical mutagens (e.g., UV light, ionizing radiation, (gamma, beta and alpha radiation, x-rays), biochemical mutagens (e.g., restriction enzymes, DNA repair mutagens, DNA repair inhibitors, and error-prone DNA polymerases and replication proteins), and the like. The mutagenic changes in DNA sequence can occur as a direct consequence of the mutagen/DNA interaction. Alternatively DNA repair mechanisms induced in response to damage inflicted by the mutagen may participate in implementing mutations.

In certain embodiments, chemical mutagenesis is used to induce mutation in one or more genes in the target cell or organism. An example of a chemical mutagen commonly used to mutate cells and organisms is N-ethyl-N-nitrosourea (ENU). Other examples of chemical mutagens useful in the present invention include, but are not limited to, ethyl-methanesulphonate (EMS) and ICR191. Many other chemical mutagens are known in the art and are useful in the present invention (see, e.g, Friedberg et al., 1995) incorporated herein by reference for teaching chemical mutagens and their use in inducing gene mutation in various cells and organisms. One having ordinary skill in the art will recognize that the mutation may be a deletion mutation, an insertion mutation, a frameshift mutation, a nonsense mutation, a missense mutation or a splicing mutation.

The utility of transposon insertional mutagenesis techniques for disruption and inactivation of genes has been demonstrated and is well known in the art. In *Drosophila*, a number of techniques have been developed for insertional mutagenesis using the P-element transposon. Techniques that produce collections of P-element transposon induced recessive lethal mutations (P-lethals) are particularly suitable for rapid identification of novel, essential genes in *Drosophila* (Cooley et al., 1988; Spralding et al., 1995; Oh et al., 2003. Since the sequences of the P-element and the *Drosophila* genome are known, it is usually possible to rapidly identify the transcription unit that a P-element has disrupted by sequencing from one or both ends of the P-element insertion into the sequences flanking the insertion. In the present invention, disruption of the *Drosophila* gene-of-interest does not result in lethality when homozygous, but does result in resistance to the lethal effects of spinosyn or its derivatives. The mutation of this gene indicates that compounds which affect the encoded subject protein will be effective insecticidal compounds and that this protein class is an excellent target for pesticidal screening and discovery. Additionally, compounds that affect this class of proteins could have therapeutic applications.

Spinosyn resistance phenotypes (including spinosyn derivative resistance phenotypes) can also be generated by co-suppression methods (Bingham, 1997; Smyth, 1997; Que and Jorgensen, 1998). Co-suppression is a phenomenon of reduced gene expression produced by expression or injection of a sense strand RNA corresponding to a partial segment of the gene of interest. Co-suppression effects have been employed extensively in plants and *C. elegans* to generate loss-of-function phenotypes, and there is a single report of co-suppression in *Drosophila*, where reduced expression of the Adh gene was induced from a white-Adh transgene using co-suppression methods (Pal-Bhadra et al., 1997).

Another method for generating spinosyn resistance phenotypes is by double-stranded RNA interference (dsRNAi). This method is based on the interfering properties of double-stranded RNA derived from the coding regions of a gene, and has proven to be of great utility in genetic studies of *C. elegans* (Fire et al., 1998), and can also be used to generate loss-of-function phenotypes in *Drosophila* (Kennerdell and Carthew, 1998; Misquitta and Patterson, 1999). In one example of this method, complementary sense and antisense RNAs derived from a substantial portion of a gene of interest, such as a subject gene, are synthesized in vitro. The resulting sense and antisense RNAs are annealed in an injection buffer, and the double-stranded RNA injected or otherwise introduced into animals (such as in their food or by soaking in the buffer containing the RNA). Progeny of the injected animals are then inspected for phenotypes of interest (PCT publication no. WO99/32619).

Additional methods that can be used for generating loss-of-function, i.e., spinosyn resistance phenotypes, include use of peptide aptamers that act as dominant inhibitors of protein function (Kolonin and Finley, 1998; Xu et al., 1997; Hoogenboom et al., 1998), RNA aptamers (Good et al., 1997; Ellington et al., 1995; Bell et al., 1998; Shi et al., 1999) and intrabodies (Chen et al., 1994; Hassanzadeh et al., 1998a and 1998b).

Intracellularly expressed antibodies, or intrabodies, are single-chain antibody molecules designed to specifically bind and inactivate target molecules inside cells. Intrabodies have been used in cell assays and in whole organisms such as *Drosophila* (Chen et al., 1994; Hassanzadeh et al., 1998a and 1998b). Inducible expression vectors can be constructed with intrabodies that react specifically with a subject protein. These vectors can be introduced into model organisms and studied in the same manner as described above for aptamers.

Mutated organisms can be screened for a desired phenotype, i.e., resistance to a spinosyn and the gene that gives rise to the desired phenotypes can be selected, identified, and characterized e.g., cloned, sequenced, mapped, etc. to identify the organisms, i.e., mutated organisms according to this aspect of the invention.

One more aspect of the present invention is a vector comprising: (a) an antisense nucleotide sequence substantially complementary to (1) a corresponding portion of one strand of a DNA molecule which has at least 50% identity, preferably at least 60% identity, particularly at least 70% identity, more preferably at least 80% identity and especially 90%, 91%, 92%, 93%, 94%, 95%, 96%, 97%, 98%, 99% and 100% identity to SEQ ID NO. 15 encoding a receptor subunit; and (b) regulatory sequences operatively linked to the antisense nucleotide sequence such that the antisense nucleotide sequence is expressed in a cell into which it is transformed, and wherein the transformed cell exhibits a reduced response to a spinosyn relative to an untransformed cell.

Antisense molecules can be complementary to an entire DNA molecule encoding the receptor subunit, i.e. of the same nucleotide length as the entire molecule. It may be desirable, however, to work with a shorter molecule. In this instance, fragments of the entire antisense molecule can be used. Suitable fragments are capable of hybridizing to the mRNA encoding the entire molecule, and preferably consist of at least twenty nucleotides. These antisense molecules and fragments thereof can be used to reduce steady state levels of a receptor subunit gene product of *Drosophila melanogaster* by introducing into cells an RNA or single-stranded DNA molecule that is complementary to the mRNA of the receptor subunit gene product (i.e. by introducing an antisense molecule). The antisense molecule can base-pair with the mRNA of the receptor subunit gene product, preventing translation of the mRNA into protein. Thus, an antisense molecule to the receptor subunit of *Drosophila melanogaster* can prevent translation of mRNA encoding the receptor subunit into a functional receptor.

More particularly, an antisense molecule complementary to mRNA encoding a receptor subunit, or a fragment thereof, can be used to decrease expression of a functional receptor subunit of *Drosophila melanogaster*. A cell with a first level of expression of a functional receptor subunit is first selected, and then the antisense molecule (or fragment thereof) is introduced into the cell. The antisense molecule (or fragment thereof) blocks expression of the receptor subunits of *Drosophila melanogaster*, resulting in a second level of expression of a functional receptor subunit of *Drosophila melanogaster* in the cell. The second level is less than the initial first level.

Typically, transgenic animals are created that contain gene fusions of the coding regions of a subject gene (from either genomic DNA or cDNA) or genes engineered to encode antisense RNAs, co-suppression RNAs, interfering dsRNA, RNA aptamers, peptide aptamers, or intrabodies operably joined to a specific promoter and transcriptional enhancer whose regulation has been well characterized, preferably heterologous promoters/enhancers (i.e. promoters/enhancers that are non-native to a subject pathway genes being expressed).

Methods are well known for incorporating exogenous nucleic acid sequences into the genome of animals or cultured cells to create transgenic animals or recombinant cell lines. For invertebrate animal models, the most common methods involve the use of transposable elements. There are several suitable transposable elements that can be used to incorporate nucleic acid sequences into the genome of model organisms. Transposable elements are particularly useful for inserting sequences into a gene of interest so that the encoded protein is not properly expressed, creating a "knock-out" animal having a loss-of-function phenotype. Techniques are well-established for the use of P element in *Drosophila* (Rubin and Spradling, 1982; U.S. Pat. No. 4,670,388) and Tc1 in *C. elegans* (Zwaal et al., 1993; Epstein and Shakes, 1995). Other Tc1-like transposable elements can be used such as minos, mariner and sleeping beauty. Additionally, transposable elements that function in a variety of species, have been identified, such as PiggyBac (Thibault et al., 1999), hobo, and hermes.

In addition to creating loss-of-function phenotypes, transposable elements can be used to incorporate the gene of interest, or mutant or derivative thereof, as an additional gene into any region of an animal's genome resulting in mis-expression (including over-expression) of the gene. A preferred vector designed specifically for misexpression of genes in transgenic *Drosophila*, is derived from pGMR (Hay et al., 1994), is 9 Kb long, and contains: an origin of replication for *E. coli*; an ampicillin resistance gene; P-element transposon 3' and 5' ends to mobilize the inserted sequences; a White marker gene; an expression unit comprising the TATA region of hsp70 enhancer and the 3' untranslated region of a-tubulin gene. The expression unit contains a first multiple cloning site (MCS) designed for insertion of an enhancer and a second MCS located 500 bases downstream, designed for the insertion of a gene of interest. As an alternative to transposable elements, homologous recombination or gene targeting techniques can be used to substitute a gene of interest for one or both copies of the animal's homologous gene. The transgene can be under the regulation of either an exogenous or an endogenous promoter element, and be inserted as either a minigene or a large genomic fragment. In one application, gene function can be analyzed by ectopic expression, using, for example, *Drosophila* (Brand et al., 1994) or *C. elegans* (Mello and Fire, 1995).

Examples of well-characterized heterologous promoters that may be used to create the transgenic animals include heat shock promoters/enhancers, which are useful for temperature induced mis-expression. In *Drosophila*, these include the hsp 70 and hsp83 genes, and in *C. elegans*, include hsp 16-2 and hsp 16-41. Tissue specific promoters/enhancers are also useful, and in *Drosophila*, include eyeless (Mozer and Benzer, 1994), sevenless (Bowtell et al., 1991), and glass-responsive promoters/enhancers (Quiring et al., 1994) which are useful for expression in the eye; and enhancers/promoters derived from the dpp or vestigal genes which are useful for expression in the wing (Stachling-Hampton et al., 1994; Kim et al., 1996). Finally, where it is necessary to restrict the activity of dominant active or dominant negative transgenes to regions where the pathway is normally active, it may be useful to use endogenous promoters of genes in the pathway, such as a subject protein pathway gene.

In *C. elegans*, examples of useful tissue specific promoters/enhancers include the myo-2 gene promoter, useful for pharyngeal muscle-specific expression; the hlh-1 gene promoter, useful for body-muscle-specific expression; and the mec-7 gene promoter, useful for touch-neuron-specific gene expression. In a preferred embodiment, gene fusions for directing the mis-expression of a subject pathway gene are incorporated into a transformation vector which is injected into nematodes along with a plasmid containing a dominant selectable marker, such as rol-6. Transgenic animals are identified as those exhibiting a roller phenotype, and the transgenic animals are inspected for additional phenotypes of interest created by mis-expression of a subject pathway gene.

In *Drosophila*, binary control systems that employ exogenous DNA are useful when testing the mis-expression of genes in a wide variety of developmental stage-specific and tissue-specific patterns. Two examples of binary exogenous regulatory systems include the UAS/GAL4 system from yeast (Hay et al., 1997; Ellis et al., 1993; Brand and Perrimon, 1993) and the "Tet system" derived from *E. coli* (Bello et al., 1998).

Dominant negative mutations, by which the mutation causes a protein to interfere with the normal function of a wild-type copy of the protein, and which can result in loss-of-function or reduced-function phenotypes in the presence of a normal copy of the gene, can be made using known methods (Hershkowitz, 1987).

In one aspect of the invention, stably transformed transgenic fish are provided. In one embodiment, a transgenic fish has a genome which has stably-integrated, or otherwise incorporated, therein an introduced receptor subunit gene operably linked to a promoter. The promoter is preferably an organ- or tissue-specific (including cell-specific) promoter or a promoter that can be regulated in a specific tissue. The receptor subunit gene is typically from an animal other than a fish and may advantageously be part of a recombinant vector as further described herein. Preferably the receptor subunit gene is an invertebrate receptor subunit. Such fish may form a stable fish line in that they have the capacity to reproduce and pass their genetic information relating to the receptor subunit to their progeny.

A wide variety of fish may be utilized in the invention. Exemplary fish include teleost fish, such as zebrafish. Zebrafish, in particular, may be advantageously utilized as compared to other animal models. For example, zebrafish are amenable to genetic screens, modifier screens, and chemical screens; develop rapidly ex-utero; are transparent for much of their life cycle and produce large clutches of offspring weekly. Zebrafish can be raised in relatively small facilities (housing up to about 54 adult fish in a single 9 liter tank), and can reliably produce offspring in large quantities, with each mature female typically laying 100 to 300 eggs per week. These eggs are fertilized externally, and the embryos are transparent allowing the early development of hematopoietic tissues and other organ and tissue systems to be directly observed using only a dissecting microscope. Embryonic development is extremely rapid with most organ systems including blood cell formation being fully developed by 5 days post fertilization. Full reproductive maturation is reached by about 3 months.

The vector includes a gene encoding a receptor subunit operably linked to a promoter. Preferably the promoter is an organ- or tissue-specific promoter.

Since most mammalian promoters are found not to work well in fish, then the genomic regulatory sequences of the zebrafish, fugu or other fish species often must be specifically cloned upstream, within, and downstream of the coding sequence of interest, which may be accomplished by procedures routine to those skilled in the art. Similar procedures may be utilized for construction of other, e.g., zebrafish, organ- and tissue-specific promoters, which are well known to those of skill in the art.

The transgene may be included in a vector for delivery. A vector, as used herein and as known in the art, refers to a nucleic acid construct that includes genetic material designed to direct transformation (i.e., the process whereby genetic material of an individual cell is altered by incorporation of exogenous DNA into its genome) of a targeted cell. A vector may contain multiple genetic elements positionally and sequentially oriented, i.e., operably linked with other necessary or desired elements such that the nucleic acid in a cassette can be transcribed and, if desired, translated in the microinjected, single-cell fertilized embryo.

Recombinant expression vectors may be constructed by incorporating the above-recited nucleotide sequences within a vector according to methods well known to the skilled artisan and as described in numerous publications.

A wide variety of vectors are known that have use in the invention. Suitable vectors include plasmid vectors, viral vectors, including retrovirus vectors (e.g., see Miller et al., 1993), adenovirus vectors (e.g., see Erzurum, et al., 1993; Zabner, et al., 1994; and Davidson, et al., 1993) adeno-associated virus vectors (e.g., see Flotte, et al., 1993), herpesvirus vectors (e.g., see Anderson, et al., 1993), and lentivirus vectors (e.g., see Lever, 2000). The vectors may include other known genetic elements necessary or desirable for efficient expression of the nucleic acid in a specified host cell, such as the transgenic fish host cells described herein, including regulatory elements. For example, the vectors may include a promoter, including one that is specific to organ- or tissue-specific as described herein and any necessary enhancer sequences that cooperate with the promoter to achieve transcription of the gene. By "enhancer" is meant nucleotide sequence elements which can stimulate promoter activity in a cell, such as a transgenic fish host cell described herein. The vectors may be in, for example, a linearized form.

Nucleotide sequence may also be fused to a nucleotide sequence encoding a reporter gene product so that a fusion protein will be formed, and whose presence and or location may be visualized or otherwise identified. The terms "encoding" and "coding" refer to the process by which a nucleotide sequence, through the mechanisms of transcription and translation, provides the information to a cell from which a series of amino acids can be assembled into a specific amino acid sequence to produce a polypeptide. As one example of such a nucleotide sequence, a nucleotide sequence encoding GFP may be advantageously utilized in the invention so that areas of the developing embryo and/or hatched or otherwise mature fish will fluoresce upon expression of the fusion protein. Alternatively, other reporter gene products may be utilized, including luciferase, beta-galactosidase, chloramphenicol acytransferase, beta-glucuronidase and alkaline phosphatase. Assays for determining the presence, and including determining the activity or amount, of the reporter gene products described herein are known to the art and are discussed in, for example, Current Protocols in Molecular Biology (Ausubel et al., eds., John Wiley & Sons), which is regularly and periodically updated. Further descriptions of assays for the reporter gene products discussed herein may be found, for example, in the following publications: for luciferase, see Nguyen, V. T. et al. (1988); for beta-galactosidase, see, e.g., Martin, C. S., et al., 1997; Jain and Magrath, 1991); for beta-galactosidase, beta-glucuronidase and alkaline phosphatase see, for example, Bronstein, et al. (1994); for chloramphenical acetyl-transferase, see Cullen (1987); Gorman, C. et al., (1982); Miner et al. (1988); Sleigh (1986); Hruby and Wilson (1992).

In yet another aspect of the invention, the gene is preceded by a reporter gene, such as a fluorescent protein gene (e.g., GFP, RFP, BFP, YFP, or dsRED2) or a luciferase protein gene, comprising a strong transcriptional stop-site, which is flanked by site specific recombinase recognition sites (e.g., Flox, Lox, or FRT-sites). A ubiquitous gene promoter (e.g., EF1-alpha or beta-actin) may drive expression of the "Loxed," "Floxed" or "FRPed" reporter gene. A second gene product (e.g., a receptor subunit gene) is adjacent to the reporter gene but is not expressed in the absence of recombinase protein expression because of the strong transcription stop-site within reporter gene. However, when the recombinase protein expression is activated in the cells, the Loxed, Floxed, or FRPed reporter gene product is excised, and the second gene is juxtaposed to the ubiquitous gene promoter. Additionally, tissue-specific recombination may be facilitated by laser-activation of a heat-shock inducible site-specific recombinase transgene through use of a laser. Laser activation may be targeted to individual cells during embryologic development.

In yet another aspect of the invention, methods of making a transgenic fish are provided herein. In one embodiment, a method includes introducing into a fertilized fish egg (i.e., including a fish embryo) or an unfertilized fish egg nucleic acid including a invertebrate receptor subunit operably linked to a promoter. The nucleic acid may be part of a vector described herein. When a fertilized fish egg is used, the method includes developing the fish embryo into a transgenic fish. When the gene encoding the nicotinic receptor subunit is introduced into a non-fertilized egg, the method includes fertilizing the egg and developing the fish embryo into a transgenic fish. The nucleic acid construct may be introduced into the egg by a variety of methods known to the art, including mechanical methods, chemical methods, lipophilic methods, retroviral infection methods, and electroporation. Exemplary mechanical methods include, for example, microinjection. Exemplary chemical methods include, for example, use of calcium phosphate or DEAE-Dextran. Exemplary lipophilic methods include use of liposomes and other cationic agents for lipid-mediated transfection. Such methods are generally well known to the art and many of such methods are described in, for example, Gene Transfer Methods: Introducing DNA into Living Cells and Organisms, (Norton and Steel, 2000); and Current Protocols in Molecular Biology (Ausubel et al.,), which is regularly and periodically updated. Microinjection techniques involving fish are further more fully described in, for example, Chen and Powers (1990) and Fletcher and Davis (1991). Electroporation techniques involving fish are further more fully described in, for example, Powers et al. (1992) and Lu et al. (1992). Techniques for introducing DNA into fish eggs or embryos by infection with retroviral vectors, such as pantropic retroviral vectors, are further described in, for example, Burns, J. C., et al. (1993).

The vector or other nucleic acid comprising the transgene may be introduced into an unfertilized egg or a fertilized egg at a desired stage of development. Multiple vectors, each encoding different transgenes as described herein may be used. When using a fertilized egg, or embryo, it is preferred to introduce the nucleic acid into the embryo (i.e., at the one-cell stage of development). However, the nucleic acid may also be administered at later stages of development, including the two-cell stage, four-cell stage, etc. Therefore, the nucleic acid may be introduced into the morula, blastula, etc. At least one isolated nucleic acid molecule incorporating the above-described transgenic construct is introduced into the zygote. Additionally, when the nucleic acid is introduced into an egg at later stages of development, at least one isolated nucleic acid molecule incorporating the above-described transgenic construct is introduced into at least one cell of the, for example, morula, blastula, etc.

Fish eggs may be obtained from the appropriate fish by standard methods. Many of the fish may be purchased commercially from, for example, pet stores. Fertilized eggs may be obtained by methods known to the art. For example, a desired number of appropriately aged fish, such as about three to about twelve month old fish, with a desired ratio of females to males (such as about 2:1) may be placed in an appropriately sized container, such as a tank. Eggs may be collected by, for example, placing the fish in a nuptial chamber in the tank for an appropriate time after mating, such as about 10 to 60 minutes. Such methods are described in, for example, Culp et al. (1991). Alternatively, fish eggs may be artificially fertilized by methods known to the skilled artisan. One skilled in the art is familiar with other methods of obtaining such fertilized fish eggs.

After introducing the nucleic acid construct into the fish egg, the fish egg or embryo is provided with an environment conducive to development into an adult fish. Such an environment may include, for example, growth at 28.5° C. in E3 egg water for 15 days followed by introduction into circulating system water by day 16 (Westerfield, 2000).

Transgenic fish produced as described herein may be identified by common procedures known to the art, including dot blot and Southern blot hybridization of genomic DNA. Briefly, such methods involve isolation of genomic DNA from tissues of the fish, digestion of DNA with restriction enzymes and Southern blot hybridization of the digested DNA products as described in, for example, Chen, T. T. et al (1996). A preliminary screen may be accomplished by isolating genomic DNA from a piece of fin tissue, amplifying the transgenic sequence by the polymerase chain reaction and Southern blot analysis of the amplified products as described in Lu et al. (1992) and Chen et al. (1993). Additionally, if a nicotinic receptor subunit-fluorescent fusion protein, including a receptor subunit-GFP fusion protein, is encoded by the introduced nucleic acid, a visual preliminary screen for fluorescence may be used.

The transgenic fish produced preferably has the transgene stably integrated into its genome. This means that the transgene is integrated into the genome of the fish as opposed to being extrachromosomal. Transgenic fish are typically contacted with the test drug or agent at a desired time after hatching. In other forms of the invention, the fish embryo contained within the fish egg may be contacted with the test agent.

A DNA fragment encoding a receptor subunit can be integrated into the genome of the transgenic mouse by any standard method well known to those skilled in the art. Any of a variety of techniques known in the art can be used to introduce the transgene into animals to produce the founder lines of transgenic animals (see, for example, Hogan et al. 1986 and 1994; U.S. Pat. Nos. 5,602,299; 5,175,384; 6,066,778; and 6,037,521). Such techniques include, but are not limited to, pronuclear microinjection (U.S. Pat. No. 4,873,191); retrovirus mediated gene transfer into germ lines (Van der Putten et al. 1985); gene targeting in embryonic stem cells (Thompson et al., 1989); electroporation of embryos (Lo, 1983); and sperm-mediated gene transfer (Lavitrano et al. 1989)).

For example, embryonal cells at various developmental stages can be used to introduce transgenes for the production of transgenic animals. Different methods are used depending on the stage of development of the embryonal cell. The zygote is a good target for micro-injection, and methods of microinjecting zygotes are well known to (see U.S. Pat. No. 4,873,191). In the mouse, the male pronucleus reaches the size of approximately 20 micrometers in diameter which allows reproducible injection of 1-2 picoliters (pl) of DNA solution. The use of zygotes as a target for gene transfer has a major advantage in that in most cases the injected DNA will be incorporated into the host genome before the first cleavage (Brinster, et al. 1985). As a consequence, all cells of the transgenic non-human animal will carry the incorporated transgene. This will in general also be reflected in the efficient transmission of the transgene to offspring of the founder since 50% of the germ cells will harbor the transgene. Microinjection of receptor subunit nucleic acid fragments into pronuclei will generate a transgenic mouse.

The transgenic animals of the present invention can also be generated by introduction of the targeting vectors into embryonal stem (ES) cells. ES cells are obtained by culturing pre-implantation embryos in vitro under appropriate conditions (Evans et al. 1981; Bradley et al. 1984; Gossler et al. 1986; and Robertson et al. 1986). Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (reviewed in Jaenisch, 1988). Prior to the introduction of transfected ES cells into the blastocoel, the transfected ES cells can be subjected to various selection protocols to enrich for ES cells that have integrated the transgene if the transgene provides a means for such selection. Alternatively, PCR can be used to screen for ES cells that have integrated the transgene. This technique obviates the need for growth of the transfected ES cells under appropriate selective conditions prior to transfer into the blastocoel.

In addition, retroviral infection can also be used to introduce transgenes into a non-human animal. The developing non-human embryo can be cultured in vitro to the blastocyst stage. During this time, the blastomeres can be targets for retroviral infection (Janenich, 1976). Efficient infection of the blastomeres is obtained by enzymatic treatment to remove the zona pellucida (Hogan et al., 1986). The viral vector system used to introduce the transgene is typically a replication-defective retrovirus carrying the transgene (Jahner et al., 1985); Van der Putten, et al., 1985)). Transfection is easily and efficiently obtained by culturing the blastomeres on a monolayer of virus-producing cells (Van der Putten et al., 1985; Stewart et al., 1987). Alternatively, infection can be performed at a later stage. Virus or virus-producing cells can be injected into the blastocoele (Jahner et al., 1982). Most of the founders will be mosaic for the transgene since incorporation occurs only in a subset of cells which form the transgenic animal. Further, the founder can contain various retroviral insertions of the transgene at different positions in the genome, which generally will segregate in the offspring. In addition, it is also possible to introduce transgenes into the germline by intrauterine retroviral infection of the midgestation embryo (Jahner et al., 1982). Additional means of using retroviruses or retroviral vectors to create transgenic animals known to the art involves the micro-injection of retroviral particles or mitomycin C-treated cells producing retrovirus into the perivitelline space of fertilized eggs or early embryos (WO 90/08832; Haskell and Bowen, 1995).

A DNA fragment comprising a cDNA encoding a receptor subunit polypeptide can be microinjected into pronuclei of single-cell embryos in non-human mammals such as a mouse. The injected embryos are transplanted to the oviducts/uteri of pseudopregnant females and finally transgenic animals are obtained.

Once the founder animals are produced, they can be bred, inbred, outbred, or crossbred to produce colonies of the particular animal. Examples of such breeding strategies include but are not limited to: outbreeding of founder animals with more than one integration site in order to establish separate lines; inbreeding of separate lines to produce compound transgenics that express the transgene at higher levels because of the effects of additive expression of each transgene; crossing of heterozygous transgenic mice to produce mice homozygous for a given integration site to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the physiological effects of expression.

The present invention provides transgenic non-human mammals that carry the transgene in all their cells, as well as animals that carry the transgene in some, but not all their cells, that is, mosaic animals. The transgene can be integrated as a single transgene or in concatamers, for example, head-to-head tandems or head-to-tail tandems.

The transgenic animals are screened and evaluated to select those animals having a phenotype wherein the receptor subunit is expressed. Initial screening can be performed using, for example, Southern blot analysis or PCR techniques to analyze animal cells to verify that integration of the transgene has taken place. The level of mRNA expression of the transgene in the cells of the transgenic animals can also be assessed using techniques which include, but are not limited to, Northern blot analysis of tissue samples obtained from the animal, in situ hybridization analysis, and reverse transcriptase-PCR (rt-PCR). The transgenic non-human mammals can be further characterized to identify those animals having a phenotype useful in methods of the invention.

In the screening methods of the subject invention, a quantity of a candidate agent is administered to the organism, e.g., *Drosophila*. Following administration, the affect of the candidate agent on the organism, e.g., fly is determined, typically by comparison with a control (e.g., a transgenic or wild type fly to which the candidate agent has not been administered). For flies, the candidate agent is generally orally administered by mixing the agent into the fly nutrient medium, e.g. water, aqueous solution with additional nutrient agents, etc., and placing the medium in the presence of the fly, (either the larva or adult fly, usually the adult fly) such that the fly feeds on the medium. Methods for administering the agent to other organisms are readily available to those having ordinary skill in the art. Generally a plurality of assay mixtures are run in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate compounds are tested in parallel using a large number of organisms. By "large number" is meant a plurality, where plurality means at least 10 to 50, usually at least 100, and more usually at least 1000, where the number of may be 10,000 or 50,000 or more, but in many instances will not exceed 5000.

The subject methods find use in the screening of a variety of different potentially insecticidal candidate compounds. Candidate compounds encompass numerous chemical classes, though typically they are organic molecules, preferably small organic compounds having a molecular weight of more than 50 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including, but not limited to: peptides, saccharides, fatty acids, steroids, purines, pyrimidines, derivatives, structural analogs or combinations thereof.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological compounds may be subjected to directed or random chemical modifications, such as acylation, alkylation, esterification, amidification, etc. to produce structural analogs. New potential pesticidal or therapeutic compounds may also be created using methods such as rational drug design or computer modeling.

The above screening methods may be part of a multi-step screening process of evaluating candidate compounds for their efficacy (and safety) as insecticides. In multi-step screening processes of the subject invention, a candidate compound or library of compounds is subjected to screening in the transgenic organisms of the subject invention. In addition, a pre in vivo screening step may be employed, in which the compound is first subjected to an in vitro screening assay for its potential as an insecticidal agent. Any convenient in vitro screening assay may be employed, where a variety of suitable in vitro screening assays are known to those of skill in the art.

Also provided by the subject invention are kits for use in performing the subject screening methods. The subject kits include the organisms of the subject invention, or a means for producing such organisms, e.g. a male and female organisms of the subject invention, vectors carrying requisite genes, such as the transgene, a transposase gene, GAL4, etc. The flies may be housed in appropriate container(s), e.g. vials. The subject kits may also comprise a nutrient medium for the animals, e.g. Drosophila medium. Screening methods utilizing direct comparison of PCR-based monitoring for resistance in Drosophila populations with insecticide bioassay are available to those skilled in the art. Aronstein, K et al. (1993).

EXAMPLES

Cloning of Drosophila Nicotinic Acetylcholine Alpha-6 Subunit

Poly A+ mRNA was isolated from frozen Drosophila heads using FastTrack 2.0 mRNA isolation kit (Invitrogen, Carlsbad, Calif.). Drosophila heads (0.326 g) and 15 ml lysis buffer were added to a Dounce homogenizer, 10 strokes were used to achieve lysis. Subsequently, kit instructions were followed and the final mRNA pellet was resuspended in 25 µl elution buffer. An A260/A280 reading was performed using 5 µl of the mRNA in 200 µl elution buffer. The mRNA concentration was 0.139 µg/µl for a total recovery of 3.475 µg. First strand cDNA was synthesized using the Invitrogen cDNA cycle kit (Invitrogen, Carlsbad, Calif.) in a 20 µl reaction and 3.5 µl of the mRNA (0.4865 µg mRNA) and following the kit instructions. PCR was performed in 25 µl reactions using the FailSafe PCR kit (Epicentre, Madison, Wis.) as follows: 1 µl cDNA, 2.5 µl of each primer having SEQUENCE ID NOS. 3 and 4 at 10 pM/µl, 0.5 µl FailSafe enzyme, 12.5 µl 2× FailSafe PCR mix (A through L) and 5 µl H2O. The reactions were performed in a PerkinElmer Cetus DNA thermal cycler as follows: 95° C./30 seconds, 55° C./30 seconds and 72° C./2 min for 30 cycles. 5 µl of each reaction was analyzed in a 1% agarose/TBE gel. Reactions using pre-mixes A, D and G yielded a product of the expected 1497 bp. The remaining 20 µl of each reaction was run in a preparative 1% agarose gel and the resulting bands were excised and purified from the gel using Qiaex II (Qiagen, Valencia, Calif.). Purified PCR products were ligated into pCR2.1-TOPO and transformed into TOP10 cells as described by the manufacturer Invitrogen, Carlsbad, Calif.). Plasmid DNA was isolated from 18 clones for each PCR product using Wizard Plus SV mini-prep kit (Promega, Madison, Wis.). PlasmidDNA was analyzed by digestion with Eco RI resulting in three restriction patterns; two fragments of 932 bp+565 bp, a single band of 1497 bp or a slightly larger single band. Sequencing of several clones revealed splice variants resulting from variable splicing of exons 3 and 8 (Grauso et al., 2002). The single restriction fragments identified in the Eco RI digests are a result of the absence of the internal Eco RI site as a result of RNAi editing (Grauso et al. 2002). The Drosophila 30D gene was removed from pCR2.1-TOPO as a Bam HI fragment and subcloned into pAcP(+)IE1-3 (Novagen, Madison, Wis.) and pGH19 (Liman et. al., 1992) using standard molecular techniques.

Cloning of Drosophila Nicotinic Acetylcholine Alpha-5 Subunit

Synthesis of first strand cDNA was performed using Superscript II first strand synthesis kit (Invitrogen, Carlsbad, Calif.) and Drosophila embryo mRNA as template (Clontech, Palo Alto (CA). PCR was performed using FailSafe PCR kit (Epicentre, Madison, Wis.) with primers having sequence ID numbers 5 and 6 and 2× reaction mixes A-F with the following cycling conditions; 95° C./3 minute denaturation followed by 30 cycles of 95° C./30 seconds, 55° C./30 seconds, 72° C./2.5 minutes followed by a final 10 minute extension at 72° C. A product of the expected 2440 bp was amplified in reactions A and D. The PCR products were ligated into pCRBluntII-TOPO and several clones were sequenced. One clone having SEQ ID NO. 1 was identified which contained only 3 base changes from NCBI accession No. AF272778. These nucleotide changes resulted in 2 amino acid substitutions which were I-V at position 603 (relative to M start) and I-M at 795, both of which are conservative amino acid substitutions. The gene was excised from pCRBluntII-TOPO as an Xba I fragment and subcloned into pAcP(+)IE1-3 and pGH19 using standard molecular techniques.

Cloning of Drosophila Nicotinic Acetylcholine Alpha-7 Subunit

First strand cDNA was synthesized from Drosophila larval mRNA (Clontech, Palo Alto (CA) using the Superscript II first stand synthesis kit (Invitrogen, Carlsbad, Calif.). PCR was performed using ThermalAce PCR kit (Invitrogen, Carlsbad, Calif.), primers having sequence ID numbers 7 and 8 and the following cycling conditions using a gradient block; 95° C./3 min followed by 30 cycles of 95° C./30 seconds, 45° C., 53.3° C. or 60° C./30 seconds, 74° C./2 minutes followed by a 74° C. extension for 10 minutes. Each reaction gave the expected 1633 by product. The product form the 60° C. annealing temperature reaction was ligated into pCRBluntII-TOPO and a clone containing the correct size insert was identified and sequenced. A single base change from C to T was identified which resulted in a premature stop codon at position 1378 relative to the ATG start. QuickChange II site directed mutagenesis kit (Stratagene, La Jolla, Calif.) was used to revert the T back to C. The final sequence having SEQ ID NO. 2 matched closely that of NCBI accession No. AJ554210 except for a lysine to threonine at amino acid 311 and the C-terminus which has the amino acid sequence of FP in place of VSGVRG as in the AJ554210 clone. The gene was excised from pCRBluntII-TOPO as an Xba I fragment and subcloned into pAcP(+)IE1-3 and pGH19 using standard molecular techniques.

Cloning of C. elegans ric-3

PCR product corresponding to the C. elegans ric3 gene was ligated into pCR2.1-TOPO and a clone containing the correct (1137 bp) insert was identified. PCR amplification was performed using the FailSafe PCR kit and primers having sequence ID numbers 9 and 10 to add Bam HI sites. The resulting PCR products were cloned into pCR2.1-TOPO and several clones containing the correct size insert were sequenced. A clone having the identical sequence to NCBI accession number NM 068898 was identified. The gene was excised from p2.1-TOPO as an Bam HI fragment and subcloned into pAcP(+)IE1-3 and pGH19 using standard molecular techniques.

Generation of Polyclonal Antibody to Drosophila 30D nAChR

A peptide sequence having SEQ ID NO. 11 was sent to Zymed Laboratories Inc. (South San Francisco, Calif.) for polyclonal antibody production in rabbits. Zymed had the peptide synthesized, produced polyhclonal serum in rabbits and then purified the polyclonal antibody using a column which had the peptide conjugated to the column matrix.

Functional Assay

Preparation of Host Cells

Xenopus laevis (Xenopus 1, Ann Arbor, Mich.; Nasco, Fort Atkinson, Wis.) were anesthetized by bathing in a solution of 2 g/l tricaine methane sulfonate, and oocytes were surgically removed from the frog and placed in a culture solution that consisted of 96 mM NaCl, 2 mM KCl, 1.8 mM $CaCl_2$, 1 mM $MgCl_2$, 5 mM HEPES, 2.5 mM Na-pyruvate, 100 units/ml penicillin, and 0.1 mg/ml streptomycin, pH 7.6. Oocytes were dispersed in a nominally zero $Ca^{2+}$ protease treatment solution to defolliculate the oocytes. The protease treatment solution consisted of either 88 mM NaCl, 2.5 mM KCl, 1 mM $MgCl_2$, 5 mM HEPES, 2.5 mM Na-pyruvate, 100 units/ml penicillin, and 0.1 mg/ml streptomycin, pH 7.6 plus 1.5 mg/ml collagenase IA (Sigma Chemical Co., St. Louis, Mo.). After isolation, the oocytes were thoroughly rinsed and returned to the above $Ca^{2+}$ containing culture solution and stored at 18° C.

Synthesis of cRNA for *Xenopus* Oocyte Injection

Synthesis of cRNA was performed as follows: Plasmid DNA was linearized with one of the following restriction enzymes; Not I, Xho I or Nhe I. The linearized DNA was subsequently used as template for cRNA synthesis using T7 mMessage mMachine kit (Ambion, Austin, Tex.) following the manufacturer's instructions.

Introduction of Nucleic Acid Molecules

Micropipettes for injection of cRNA into *Xenopus* oocytes were pulled on a DMZ-Universal Puller (Zeitz-Instruments, München, Germany). The cRNA to be injected was drawn up into the micropipette with negative pressure. Approximately 10-50 ng of cRNA was injected into the oocytes by applying positive pressure using a Nanoject II oocyte injector (Drummond Scientific Co., Broomall, Pa.). Nucleic acid was introduced into the oocytes as follows: (1) nicotinic acetylcholine receptor alpha-6 subunit subunit (30D) (2) nicotinic alpha-7 receptor subunit (34E); (3) nicotinic acetylcholine receptor alpha-6 subunit and *C. elegans* ric-3 (30D and ric-3); (4) nicotinic alpha-7 receptor subunit and *C. elegans* ric-3 (34E and ric-3); (5) nicotinic acetylcholine receptor alpha-6 subunit and nicotinic alpha-7 receptor subunit (30D and 34E); and, (6) nicotinic acetylcholine receptor alpha-6 subunit, nicotinic alpha-7 receptor subunit and *C. elegans* ric-3 (30D, 34E and ric-3).

Voltage Clamp Analysis

The control external solution for voltage clamp recordings consisted of 88 mM NaCl, 1 mM KCl, 0.41 mM $CaCl_2$, 2.4 mM $NaHCO_3$, 0.3 mM $Ca(NO_3)_2$, 0.82 mM $MgSO_4.7H_2O$, and 15 mM HEPES, pH 7.6. The recording chamber was continuously perfused with a gravity-fed perfusion system. Nicotine (1 mM) was added to the external solution and then added to the perfusate for 30 seconds. Then, nicotine was washed from the external solution a minimum of 10 minutes. Thereafter, spinosyn A was dissolved in dimethylsulfoxide (DMSO) and then dissolved in the external solution at a final concentration of 10 µM and then added to the perfusate for 60 seconds. Then, the spinosyn A was washed from the external solution. The final concentration of DMSO never exceeded 0.1% (v/v).

Voltage-clamp recordings were conducted 1-5 days following injection. Some recordings were performed manually using an OC-725C Oocyte Clamp (Warner Instruments, Hamden, Conn.), while most were made using a Roboocyte Automated Oocyte Recording System (Multichannel Systems, Reutlingen, Germany). For manual recordings, recording microelectrodes with final resistance of 1-5 MΩ were fabricated with a DMZ-Universal Puller (Zeitz-Instruments, München, Germany) and filled with 3 mM KCl. Standard two-electrode voltage-clamp techniques were used to record currents in response to nicotine or spinosyn A application. Oocytes were voltage clamped to −60 mV and currents induced by application of nicotine or spinosyn A were measured at peak amplitude. Data were amplified with the above described amplifiers and recorded on a computer using either AcqKnowledge hardware/software (BIOPAC Systems, Inc., Santa Barbara, Calif.) or the Roboocyte Automated Oocyte Recording System software (Multichannel Systems, Reutlingen, Germany).

Results and Discussion

The results are shown in Table 1 below.

TABLE 1

| Combination | Nicotine Response | Spinosyn A Response |
|---|---|---|
| 30D | − | − |
| 34E | + | − |
| 34E/ric-3 | + | − |
| 30D/ric-3 | + | + |
| 34E/30D | ++ | ++ |
| 34E/30D/ric-3 | ++++ | ++++ |

"−" indicates a negligible current was induced.
"+" indicates a small amplitude current.
"++" indicates a moderate amplitude current.
"++++" indicates a large amplitude current.

The descriptors "negligible," "small," "moderate," and "large" are relative terms within the dataset presented herein.

As can be seen from the above Table 1, oocytes that were injected with 30D (nicotinic acetylcholine receptor alpha-6 subunit located at 30D on chromosome 2L) cRNA alone showed neither a nicotine response nor a spinosyn A response. Oocytes that were injected with 34E (nicotinic acetylcholine receptor alpha-5 subunit located at 34E on chromosome 2L) cRNA alone or both 34E and ric-3 cRNAs showed a small amplitude nicotine response but a negligible spinosyn A response. Oocytes that were injected with 30D and ric-3 cRNAs showed a small amplitude response to either nicotine or spinosyn A. This evidences that expression of the nicotinic acetylcholine receptor alpha-6 subunit subunit together with a partner protein, i.e., an accessory protein is capable of detecting a chemical agent with the ability to influence the alpha-6 receptor. Oocytes that were injected with 34E and 30D cRNAs showed a moderate amplitude response to either nicotine or spinosyn A. This further evidences that expression of the nicotinic acetylcholine receptor alpha-6 subunit together with a partner protein, i.e., a ion channel subunit is capable of detecting a chemical agent with the ability to influence the alpha-6 receptor. Oocytes that were injected with 34E, 30D and ric-3 cRNAs showed a large amplitude response to either nicotine or spinosyn A. This further evidences that expression of the nicotinic acetylcholine receptor alpha-6 subunit together with multiple partner proteins are capable of detecting a chemical agent with the ability to influence the alpha-6 receptor.

Binding Assay

Expression of Nicotinic Acetylcholine Receptor Subunits in Insect Cells

For baculovirus mediated expression, a gene for a nicotinic acetylcholine receptor alpha-6 subunit located at 30D on chromosome 2L was cloned into the baculovirus transfer vector pAcP(+)IE1-3 (Novagen, Madison, Wis.) using standard molecular cloning techniques. For generation of recombinant virus, Sf9 cells were seeded into 6 well culture plates at $8 \times 10^5$ cells/well in 2 ml Sf900II SFM (Invitrogen, Carlsbad, Calif.) and allowed to attach at 27° C. for 1 hr. In a 12×75 mm polystyrene tube a DNA/lipid mixture was prepared by combining 86 µl sterile water, 5 µl transfer vector at 0.1 µg/µl, 5 µl BacPAK6 Bsu36 I linear DNA (Clontech, Palo Alto, Calif.) and 4 µl Bacfectin (Clontech, Palo Alto, Calif.) and this mixture was incubated at room temperature for 15 min. While the DNA/lipid mixture was incubating, the media was removed from the attached cells and replaced with 1.5 ml fresh media. The DNA/lipid mixture was then added to the cells in a dropwise manner, while gently swirling, and the cell mixture was incubated at 27° C. for 5 hrs. Then an additional 1.5 ml of Sf900II SFM was added and the cell mixture was incubated at 27° C. for another 4-5 days. The cell mixture was centrifuged for 5 min at 1000 rpm in a table top centrifuge to remove cell debris. The supernatant containing the recombinant virus (transfection media) was transferred to a clean tube and stored at 4° C.

To amplify the recombinant virus, 50 ml of Sf9 cells at a density of $1 \times 10^6$ cells/ml were added to a 125 ml disposable Erlenmeyer flask. 1 ml of the transfection media was then added to the cells and the mixture was incubated at 27° C. and 140 rpm for 48 hours. After 48 hours, the transfection mixture was centrifuged at 1000 rpm in a table top centrifuge for 5 minutes. The supernatant was transferred to a clean flask and designated $P_1$ virus stock. For nicotinic acetylcholine receptor subunit expression, 50 ml of Sf9 cells were seeded into a 125 ml Erlenmeyer flask at a density of $2 \times 10^6$ cells/ml. 1 ml of $P_1$ virus stock was added to the cells and the flask was incubated at 27° C. at 140 rpm for 24 hours. A 100 µl sample was removed from the flask for Western blot analysis to confirm the expression of the nicotinic acetylcholine receptor subunit and the remaining culture was used in binding assays.

Cloning of 30D nAChR Alpha 6 for Expression in D.Mel-2 Cells

The previously cloned *Drosophila* nAChR alpha-6 gene was PCR amplified using primers seq ID. 12 and 13 to add Spe I sites at the 5' and 3' ends. The primer seq ID. 12 added a Kozak translation initiation sequence to the 5' end to enhance expression in D.Mel-2 cells. The resulting product was ligated into pCR2.1-TOPO (Invitrogen, Carlsbad, Calif.) and sequenced. The sequence was as previously determined for the nAChR 30D, except for changes introduced by the primers. The gene was cut out of the pCR2.1-TOPO vector with Spe I and ligated into both pMT/V5-HisA and pIB/V5-HisA which had been linearized with Spe I and treated with shrimp alkaline phosphatase. Correct clones for each were identified and verified by restriction digest and sequencing. Plasmid was bulked up using the Qiagen EndoFree Maxi kit (Qiagen, Valencia, Calif.).

Cloning of C. elegans ric3 for Expression in D.Mel-2 Cells

The previously cloned *C. elegans* ric3 gene was PCR amplified using primers Seq ID 14 and Seq ID 10 to add a Kozak translation initiation signal. The resulting PCR product was ligated into pCR2.1-TOPO and sequenced. The sequence was as previously described except for the introduced Kozak sequence. The gene was isolated as a Bam HI fragment and ligated into pIB/V5-HisA and pMT/V5-HisA which had been cut with Bam HI and treated with shrimp alkaline phosphatase. Correct clones were identified and verified by restriction digest and sequencing. Plasmid was bulked up using the Qiagen EndoFree Maxi kit.

Transient Expression of *Drosophila* nAChR alpha6 in D.Mel-2 Cells

D.Mel-2 cells were seeded into 75 cm² flasks at $1.9 \times 10^7$ cells/flask in *Drosophila* SFM containing antibiotic/antimicotic and incubated overnight at 27° C. The transfection mix was prepared in 12×75 mm polystyrene tubes by mixing 1630 µl sterile water, 40 µg pIB/V5-HisA/ric3, 40 µg pIB/V5-HisA/30D and 250 µl CellFectin. The reagents were mixed gently and incubated at room temp for 15 minutes. While the transfection mix was incubating, the cells were washed with 10 ml fresh *Drosophila* SFM without antibiotics; this media was then removed from the cells and replaced with 6 ml fresh *Drosophila* SFM without antibiotics. To the transfection mix was added 4 ml *Drosophila* SFM without antibiotics and this was then transferred to the flask. The reagents were gently mixed by pipetting up and down and then incubated overnight at 27° C.

Stable Expression of *Drosophila* nAChR Alpha6 in D.Mel-2 Cells

D.Mel-2 cells were purchased from Invitrogen (Carlsbad, Calif.) and grown in disposable 125 ml shake flasks using 50 ml volume. Cells were subcultured to $3 \times 10^5$ cells/ml twice per week in *Drosophila* SFM containing 5 ml/L Antibiotic-Antimycotic (100×) (Gibco, Carlsbad, Calif.). D.Mel-2 cells were seeded into a 12-well plate at a cell density of $5 \times 10^5$ cells/well and incubated overnight at 27° C. In a 12×75 mm polystyrene tube 6 µg pIB/V5-HisA/ric3, 82 µl sterile $H_2O$ and 12 µl CellFectin (Invitrogen, Carlsbad, Calif.) were added. The sample was mixed gently and incubated at room temperature for 15 minutes. While the transfection mix was incubating, media from one well of cells was removed and replaced with 1 ml fresh media without antibiotics. After 15 minutes, the media was removed from cells. To this transfection mix, 0.5 ml media (no antibiotics) was added. This solution was then added to the cells. The mixture was incubated for 48 hrs at 27° C. After 48 hrs, the cells were scraped from the plate using a cell scraper and split into 4 wells of a 6-well plate each containing 2 ml *Drosophila* SFM with antibiotics. Cells were allowed to attach for 1 hr at 27° C.; the media was removed and replaced with 2 ml fresh media containing 25 µg/ml Blasticidin S (Invitrogen, Carlsbad, Calif.). Cells were incubated at 27° C. for 5 days. After 5 days, the cells were scraped loose from the wells and combined into one tube. Cells were spun down at 600 rpm in a tabletop centrifuge; the media was removed and the cells were resuspended into a 50 ml shake culture in fresh *Drosophila* SFM containing 25 µg/ml Blasticidin S. The cells were incubated at 27° C./140 rpm. Cells were subcultured twice weekly back to cell density of $3 \times 10^5$ cells/ml. After 4 weeks the selection was cut back to 10 µg/ml Blasticidin S. After 3 months of growth under selection, a 12 well plate was seeded at $5 \times 10^5$ cells/well and cells were incubated over night at 27° C. The following reagents were added to each of three 12×75 mm polystyrene tubes: 2 µg pMT/V5-HisA/30D, 0.15 µg pCoHygro (Invitrogen, Carlsbad, Calif.) (a 40:1 ratio of expression plasmid:selection plasmid), 89 µl sterile $H_2O$ and 12 µl CellFectin. The samples were mixed gently and incubated at room temp for 15 minutes and then transfected as described above. After 24 hrs, the media containing transfection mix was removed and replaced with 1 ml fresh media containing antibiotics. The incubation was continued at 27° C. for another 24 hrs. Cells were scraped loose from the 12-well plate (3 wells) and split into 2, 6-well plates. Cells were allowed to attach for 6 hours at which point, the media was replaced with 2 ml/well fresh media containing 200, 150, 100 or 50 µg/ml hygromycin B. The incubation was continued at 27° C.; every 4-5 days, the media was replaced with media containing hygromycin every 4-5 days. After 2 weeks of selection in the plates, the cells from the 200 µg/ml selection, were scraped loose and then gently pelleted and resuspended in 25 ml fresh media containing 200 µg/ml hygromycin B and then placed into a 125 ml shake flask. The incubation was continued at 27° C./140 rpm and the cells were allowed to continue to expand cells under selection. To induce expression of the 30D nAChR, the cells were spun down at 630 rpm for 5 minutes in a table-top centrifuge. The cells were resuspended at $2 \times 10^6$ cells/ml in fresh media without hygromycin B with the addition of copper sulphate at a final concentration of 600 μM. Cells were incubated for 24 hours at 27° C./140 rpm.

Transformed Cell Preparation

For the binding assays, insect cells and cRNA-injected Xenopus oocytes were prepared as follows: insect cells were gently spun in a room-temperature centrifuge. The supernatant was decanted and the pellet was rinsed twice in cold Storage Buffer containing 200 mM sucrose, 10 mM phosphate buffer, 1 mM EDTA, 1 mM PMSF at pH 7.2-7.4. The final pellets were diluted in the cold Storage Buffer and aliquoted. These cell aliquots were stored at −80° C. for use in the binding assay.

Xenopus oocytes were injected as previously described for the electrophysiological assay and were used intact for binding assays.

Radioligand Displacement Binding Assay

Two main radioligands were used in binding assays: the conventional α7 radioligand, [$^3$]methyllycaconitine (MLA) and [$^3$]dihydrospinosyn A (DHSA). For both radioligands, the Binding Buffer used consisted of 10 mM sodium phosphate (7.2-7.4). All experiments using D.Mel-2 cell suspensions were carried out with 50 μl of cell suspension. For Xenopus oocyte binding assays, oocytes were pooled (2-5 oocytes) and transferred to 1 ml Binding Buffer. This was followed by gently aspirating the Binding Buffer and replacing with fresh Binding Buffer twice, to wash out any residual oocyte bathing media. The final volume of buffer added to each pool of oocytes was 50-100 μl. Unlabeled nicotine and spinosyn A were formulated in 100% DMSO and 100% ethanol, respectively, at a concentration of 40 mM and sonicated (if needed) at room temperature. Subsequent dilutions were made in Binding Buffer. The final concentration of solvent was maintained at less than 0.1% in each well. 25 μl of unlabeled competing compounds were added to the cell suspensions or oocytes. Cells or cell extracts were pre-incubated with compounds for 15-30 minutes, at 10° C. (for [$^3$H] DHSA) and room-temperature for [$^3$H]MLA. The samples were gently shaken using a plate shaker. To this mixture was added 25 μl of 1-10 nM [$^3$H]MLA or [$^3$H]DHSA, in a total volume of 100 ul of Binding Buffer. Reactions were performed in triplicate in 96-well shallow-well microtiter plates and were incubated, at 10° C. (for [$^3$H]DHSA) and room-temperature for [$^3$H]MLA, while gently shaking using a plate shaker for 30-90 minutes. For the cell extracts, bound radioactivity and free radioactivity fractions were separated by gentle vacuum through GF/C glass fiber filter mats using a TomTec (CT) 96-well cell harvester. For those assays utilizing [$^3$H]DHSA, the filter mats were presoaked for 1-2 hrs. in 0.5% PEI (w/v; diluted in deionized water) to reduce nonspecific binding. In the case of the [$^3$H]MLA assays, however, the filter mats were briefly pretreated with 10 mM sodium phosphate buffer, containing 2 mg/ml of BSA (pH 7.2-7.4). Each sample was rapidly washed 3 times in ice-cold Binding Buffer. Filter mats were dried in an oven at 60° C. and the radioactivity from samples was counted for three minutes with a Wallac MicroBeta Counter (Wallac, Conn.) using Meltilex solid-scintillant (PerkinElmer, Finland).

In the case of whole oocyte binding, the reaction was terminated by the addition of ice-cold Binding Buffer, followed by 2 aspiration steps, with Binding Buffer washes in-between. The oocytes were transferred into scintillation vials containing 7 ml of scintillation cocktail (UlitmaGold MV, Packard Biosciences, CT) and vortexed before counting for 3 minutes in the a liquid scintillation counter (Tri-carb 2900TR, Packard Biosciences, CT).

Results and Discussion

TABLE 2

[$^3$H]MLA Binding in Intact Xenopus oocytes 3 days post-injection with Dmα6

| Test Compounds | % Displacement of Total Binding |
|---|---|
| 10 μM Spinosyn A | 72 |
| 1 mM Nicotine | 72 |

The results shown in Table 2 demonstrate the nicotinic nature of the Dα6-nicotinic receptor due to the significant displacement (72%) of [$^3$H]MLA, observed in the presence of nicotine. These oocyte data, which correlate with the oocyte functional data (i.e., induction of current) provide evidence for an effect of spinosyn at the Dα6-nicotinic receptor expressed in Xenopus oocytes. In addition, these data demonstrate, for the first time, the interaction of spinosyn A with the binding of [$^3$H]MLA in Dα6-nicotinic receptors, expressed in Xenopus oocytes. In addition, a dose-dependent displacement of [$^3$H]MLA in Dα6-nicotinic receptors, transiently expressed in Sf9 and S2 insect cells has been observed, suggesting that such an assay can be used for high-throughput screening to identify novel chemistries interacting with α6-nicotinic receptors.

[$^3$H]DHSA binding in D.Mel-2 cells expressing D α6 and C. elegans ric3 is much improved over the overall binding seen with [3H]MLA.

In addition, the pharmacology observed using [$^3$H]DHSA, in D.Mel-2 cells is nicotinic in nature as demonstrated by displacement by nicotine but not by muscarinic agents such as muscarine and atropine. Although displacement of [$^3$H] DHSA binding, by conventional nicotinic antagonists such as MLA and alpha-bungarotoxin can be demonstrated at higher concentrations, the overall affinity of these ligands for this receptor complex is relatively poor. Other nicotinic ligands such as imidacloprid, epibatidine, thiamethoxam, carbamylcholine and lobeline did not significantly displace [$^3$H]DHSA binding. Further characterization of this binding was conducted by evaluating the effects of a number of known spinosyn analogs in this [$^3$H]DHSA binding assay. No significant displacement was observed with the sugars rhamnose or furosemide. Nor was there significant displacement with the pseudoagylcone of spinosyn A. Spinosyn A, dihydrospinosyn A and a number of biologically active derivatives of spinosyn A were shown to cause significant displacement of [$^3$H] DHSA binding. These data further support the conclusion that this [$^3$H]DHSA binding assay is predictive of interactions of ligands with the spinosyn A binding site and thus, can be used to determine structure-activity relationships. Furthermore, these data suggest that this assay/receptor combination can be useful in the discovery of novel agents, interacting with the spinosyn target site.

Generation of a Drosophila 30D-Specific (Nicotinic Acetylcholine Receptor Alpha-6 Subunit) Polyclonal Antibody Using the align feature of the Vector NTi program, all published insect nicotinic acetylcholine receptor alpha subunit sequences were aligned. A 15 amino acid peptide was identified corresponding to amino acids 367-380 of the 30D coding region which is unique to 30D. A peptide sequence of SEQUENCE ID NO: 11, was submitted to Zymed Laboratories Inc. (San Francisco, Calif.) for generation of a peptide-specific polyclonal antibody. Expression of nicotinic alpha-6 receptor subunit in host cells was confirmed using the 30D-specific antibody as primary antibody in Western blots. This 30D-specific antibody failed to react with the proteins isolated from host cells expressing nicotinic alpha-5 receptor subunit or a chicken alpha-7 receptor subunit.

Inventive Organisms

Spinosyn A resistant *Drosophila melanogaster* were selected by two methods. In one method, homozygous male flies of the genotype cn bw dp were collected and aged 2-5 days in the absence of females. The males were starved 2-3 hours and then allowed to feed on a 40-50 mM solution of mutagen ethylmethane sulfonate (EMS) in 1% sucrose (w/v) for approximately 16 hours. Males that survived EMS treatment were mated either to females that were homozygous for a null allele of a nicotinic acetylcholine alpha-6 receptor subunit that confers resistance to spinosyn A in the homozygous state or to females of the genotype CyO/InGla (CyO confers resistance to spinosyn A). The eggs resulting from the mating were allowed to develop into adults. After aging for 2-5 days, the adults were exposed to spinosyn A through both feeding and contact by placing the flies in vials in which standard *Drosophila melanogaster* feeding media had been overlayed with a filter paper impregnated with a solution of 100 ppm spinosyn A in 5% sucrose. Individual flies were scored as resistant to spinosyn A if they exhibited few or no spinosyn A toxicity symptoms after 36-96 hours exposure to the compound. Putative spinosyn A resistant adults were crossed individually to flies with the CyO/InGla genotype for isogenizing the second chromosome. Progeny homozygous for the second chromosome from these crosses were reselected for spinosyn A resistance.

In the second method, *D. melanogaster* males homozygous for a null allele that confers spinosyn A resistance and carrying the hs-hid (heat-shock-head involution defective) transgene on the Y chromosome were mated to females homozygous for a null allele that confers spinosyn A resistance. Eggs resulting from the mating were collected and allowed to develop. After 5-6 days, the developing larvae were placed at 37° C. for 2 hours. This heat-shock treatment leads to ectopic and lethal expression of the hid gene product. Because the hs-hid construct is carried on the Y chromosome, the lethal effects of the heat-shock treatment are limited to male larvae. Thus, only female larvae develop into adults. Approximately 13,000 virgin female adult flies collected in this manner were mated with over 4,000 cn bw dp homozygous males that had been mutated with EMS as previously described. Resistant larvae were selected by collecting eggs resulting from the mating and distributing them onto media containing 0.1 ppm spinosyn A. Developing larvae were scored for resistance to spinosyn A after 3 days. Larvae scored as resistant were moved to vials containing fresh media and allowed to continue development in the absence of spinosyn A. Emerging adults were crossed to flies of the genotype CyO/InGla for isogenizing the second chromosome. Progeny homozygous for the second chromosome from this cross were reselected for spinosyn A resistance.

Approximately 10 mutant alleles, coding for a *Drosophila melanogaster* nicotinic acetylcholine alpha-6 receptor subunit that conferred resistance to spinosyn A were isolated by the two methods described. Analysis of these alleles revealed several different types of mutations. These included mutations that introduced a premature stop codon into the gene sequence, mutations resulting in single amino acid substitutions in the polypeptide encoded by the gene sequence and mutations that affected mRNA splicing. An example of an introduced premature stop codon that resulted in resistance to Spinosyn A is a mutation in the nicotinic acetylcholine receptor alpha-6 subunit having SEQ ID NO. 15 in which the CAA codon for glutamine 26 was changed to the stop codon TAA. An example of an amino acid substitution resulting in resistance to spinosyn A is a mutation in the nicotinic acetylcholine receptor alpha-6 subunit having SEQ ID NO. 15 in which the TGC codon for cysteine 168 was changed to a serine TCC codon. An example of a mRNA splice site mutation resulting in resistance to spinosyn A is a mutation in the nicotinic acetylcholine receptor alpha-6 subunit having SEQ ID NO. 15 where the splice acceptor site at the end of intron 4 has been mutated from TAGCGC to TAACGC.

21-Butenyl-Spinosyn Screen Using Mutant Flies

Ten adult *Drosophila melanogaster* flies (5 males and 5 females) of the Oregon wild-type strain and ten adult flies of a spinosyn-resistant strain were used per treatment. Two sets (of 10 flies) were set-up per treatment. Stocks of spinosyn A and a 21-butenyl-spinosyn analog were formulated at 1000 ppm in 2:1 acetone:water and then diluted to the required concentration in 10% sucrose. Vials received 500 ul of treatment (or solvent for controls) via cotton wicks (approximately ¼ inch) and flies were added to each vial and capped with a cotton plug. Flies were monitored over 72 hours post-treatment while being maintained at room-temperature with a 12:12 light:dark cycle.

Results

All flies were observed for mortality 72 hours post-treatment. At 100 ppm of spinosyn A or 21-butenyl spinosyn, all wild-type flies exhibited mortality. At the same concentration, no significant mortality was observed in the spinosyn-resistant flies. Dose-response data (i.e., $LD_{50}$) suggested that the spinosyn A resistant flies were at least 100-fold more resistant to spinosyn A when compared to wild-type flies. In addition, the spinosyn A resistant flies were >100-fold resistant (based on $LD_{50}$) to the new class of spinosyns, represented by the 21-butenyl spinosyns. These data demonstrate the utility of the spinosyn A resistant flies (i.e., target site mutants) as screens for the discovery of novel compounds that interact with the spinosyn A alpha-6 nicotinic receptor subunit.

Although preferred embodiments have been depicted and described in detail herein, it will be apparent to those skilled in the relevant art that various modifications, additions, subtractions and the like can be made without departing from the spirit of the invention and these are therefore considered to be within the scope of the invention as defined in the claims.

LIST OF REFERENCES CITED

Altschul et al., J Mol Biol 215:403-410 (1993).
Anderson et al., Cel Mol Neurobiol 13:503-515 (1993).
Aronstein et al., Pestic Biochem. Physiol 48(3):229-233 (1993).
Ashburner, In Fly Pushing: The Theory and Practice of *Drosophila melanogaster* genetics (1997) Cold Spring Harbor Press, Plainview, N.Y.
Ashburner, In *Drosophila melanogaster*: A Laboratory Manual (1989), Cold Spring Harbor, N.Y., Cold Spring Harbor Laboratory Press: pp. 299-418
Ausuble et. al., In Short Protocols in Molecular Biology, Third Edition. (1995),
Bayer et al., Meth Enzym 62:308 (1979).
Bell et al., J Biol Chem 273:14309-14314 (1998).
Bello et al., Development 125:2193-2202 (1998).
Bingham, Cell 90(3):385-387 (1997).
Bloomquist and Soderlund, Mol Pharmacol 33:543-550 (1988).
Bowtell et al., PNAS USA 88(15):6853-6857 (1991).
Bradley et al., Nature 309:255-258 (1984).
Brand and Perrimon, Development 118:401-415 (1993).
Brand et al., Methods Cell Biol 44:635-654 (1994).

Brinster et al., PNAS 82:4438-4442 (1985).
Bronstein et al., in Bioluminescence and Chemiluminescence: Fundamentals and Applied Aspects, pp. 20-23, (A. K. Campbell, et al., eds., John Wiley & Sons, 1994)
Burns et al., PNAS 90:8033-8037 (1993).
Campbell, Monoclonal Antibody Technology: Laboratory Techniques in Biochemistry and Molecular Biology, (1984).
Capecchi, Cell 22:479-488 (1980).
Chen and Powers, Trends Biotechnol 8:209-215 (1990).
Chen et al., Molec Biol Biotechnol 2:88-95 (1993).
Chen et al., Hum Gen Ther 5:595-601 (1994).
Chen et al., Biotech Ann Rev 2:205-236 (1996).
Cooley et al., Science 239(4844):1121-1128 (1988).
Creighton, Proteins. Structure and Molecular Principles. (1984).
Cullen, Methods Enzymol 152:684-704 (1987).
Culp et al., PNAS USA 88:7953-7957 (1991).
Davidson et al., Nature Genetics 3:219-223 (1993).
Deri and Adam-Vizi, J Neurochem 61:818-825 (1993).
Eldefrawi et al., FASEB J 1:262-271 (1987).
Ellington et al., Biotechnol Ann Rev 1:185-214 (1995).
Ellis et al., Development 119(3):855-865 (1993).
Engval et al., Immunol 109:129 (1972).
Epstein and Shakes, Caenorohabditis elegans: Modern Biological Analysis of an Organism (1995).
Erzurum et al., Nucleic Acids Res 21: 1607-1612 (1993).
Evan et al., Nature 292:154-156 (1981).
Fire et al., Nature 391:806-811 (1998).
Fletcher and Davis, In Genetic Engineering (1991).
Flotte et al., PNAS USA 90:10613-10617 (1993).
Friedburg et al., DNA Repair and Mutagenesis (1995).
Frohman et al., PNAS USA 85:8998 (1988).
Frohman and Martin, Technique 1:165-170 (1989).
Goding, J Immunol Meth 13:215 (1976).
Goeddel, Gene Expression Technology In Methods in Enzymology (1990).
Good et al., Gene Therapy 4:45-54 (1997).
Gorman et al., Mol Cell Biol 2:1044-1051 (1982).
Gossler et al., PNAS 83:9065-9069 (1986).
Grauso et al., Genetics 160:1519-1533 (2002).
Haskell and Bowen, Mol Reproduc Dev 40:386 (1995).
Hassanzadeh et al., FEBS Letters 16:75-80 (1998a).
Hassanzadeh et al., FEBS Letters 16:81-86 (1998b).
Hay et al., Development 120 2121-2129 (1994).
Hay et al., PNAS USA 94(10):5195-5200 (1997).
Hershkowitz, Nature 329:219-222 (1987).
Higgins and Sharp, Computer Applications BioSci 5(2):151-153 (1989).
Hogan et al., Manipulating the Mouse Embryo: A Laboratory Manual (1994).
Hogan et al., Manipulating the Mouse Embryo: A Laboratory Manual (1986).
Hoogeboom et al., Immunotechnology 4:1-20 (1998).
Hruby and Wilson, Methods Enzymol 216:369-372 (1992).
Jaenisch, Science 240:1468-1474 (1988).
Jahner et al., PNAS 82:6927-6931.
Jahner et al., Nature 298:623-628 (1982).
Jain and Magrath, Anal Biochem 199:119-124 (1991).
Janenich, PNAS 73:1260-1264 (1976).
Kenderdell and Carthew, Cell 95:1017-1026 (1998).
Kim et al., Nature 382:133-138 (1996).
Kirst et al., Tetrahedron Lett 32(37):4839-4842 (1991).
Klein et al., Nature 327:70-73 (1987).
Kolonin and Finley, PNAS USA 95:14266-14291 (1998).
Lavitrano et al., Cell 57:717-723 (1989).
Lerner, Adv. Immunol 36: 1-44 (1984)
Lever, Curr Opinion Mol Ther 2:488-496 (2000).
Liman et. al., Neuro 9(5):861-871 (1992).
Lin et al., Biotechniques 26(2):318-326 (1999).
Lo, Mol. Cell. Biol. 3:1803-1814 (1983).
Loh et al., Science 243:217-220 (1989).
Loughney et al., Cell 58:1143-1154 (1989).
Lu et al., Molec Biol Biotechnol 1:366-375 (1992).
Lutz et al., Exp Cell Res 175:109-124 (1988).
Mannino, and Gould-Fogerite, BioTechniques 6:682-690 (1988).
Martin et al., in Bioluminescence and Chemiluminescence: Molecular Reporting with Photons (1997).
McPherson, Directed Mutagenesis: A Practical Approach (1991).
Mello and Fire, Methods Cell Biol 48:451-482 (1995).
Miller, Bioessays 11:91-95 (1989).
Miller et al., Methods of Enzymology 217:581-599 (1993).
Miner et al., J Virol 62:297-304 (1988).
Misquitta and Patterson, PNAS USA 96:1451-1456 (1999).
Miyawaki et al., Nature 388(6645):882-887 (1997).
Mozer and Benzer, Development 120:1049-1058 (1994).
Needleman and Wunsch, J Mol Biol 48:443-453 (1970).
Nguyen et al., Anal Biochem 171:404-408 (1988).
Norton and Steel, In Gene Transfer Methods: Introducing DNA into Living Cells and Organisms (2000).
Oh et al., Genetics 163:195-201 (2003).
Ohara et al., PNAS USA 86:5673-5677 (1989).
Pal-Bhadra et al., Cell 90(3):479-490 (1997).
Powers et al., Molec Mar Biol Biotechnol 1:301-308 (1992).
Que and Jorgensen, Dev Genetics 22(1):100-119 (1998).
Quiring et al., Science 265:785-789 (1994).
Rauh et al., Trends Pharmacol Sci 11:325-329 (1990).
Robertson et al., Nature 322:445-448 (1986).
Romoser et al., J Biol Chem 272(20):13270-13274 (1997).
Rubin and Spradling, Science 218:348-353 (1982).
Sambrook and Russell, Molecular Cloning: A Laboratory Manual (2000).
Shi et al., PNAS USA 96: 10033-10038 (1999).
Shigekawa, and Dower, BioTechniques 6:742-751 (1988).
Sleigh, Anal Biochem 156:251-256 (1986).
Smyth, Curr Biol 7(12):793-795 (1997).
Spralding et al., PNAS USA 92:10824-10830 (1995).
St. Groth et al., J Immunol Methods 35:1-21 (1980).
Stachling-Hampton et al., Cell Growth Differ 5(6):585-593 (1994).
Sternberger et al., J Histochem Cytochem 18:315 (1970).
Stewart et al., EMBO J. 6:383-388 (1987).
Stuhmer, Methods in Enzymology 207:319-339 (1992).
Taglialatela et al., Biophys J 61:78-82 (1992).
Thibault et al., Insect Mol Biol 8(1):119-122 (1999).
Thompson et al., Cell 56:313-321 (1989).
Van der Putten et al., PNAS 82:6148-6152 (1985).
Westerfield, In The Zebrafish Book: A Guide for the Laboratory Use of Zebrafish (Danio rerio), 4th Edition (2000).
Wilcox, In Methods in Molecular Biology: Calcium Signalling Protocols (1999).
Wood, In The Nematode *C. elegans* (1988).
Wood et al., Recent Res Develop Neurochem 3(1):135-142 (2000).
Xu et al., PNAS USA 94:12473-12478 (1997).
Ye et al., Talanta 65(1):206-210 (2005).
Zabner et al., Nature Genetics 6:75-83 (1994).
Zwaal et al., PNAS USA 90:7431-7435 (1993).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the scope of the appended claims.

We claim:

1. A non-human transgenic organism comprising a heterologous polynucleotide that is at least 99% identical to SEQ ID NO: 15 that encodes a receptor subunit and results in a reduced response of the transgenic organism to a spinosyn, relative to the parental organism that does not comprise the heterologous polynucleotide that is at least 99% identical to SEQ ID NO: 15.

2. The transgenic organism of claim 1, wherein the organism is an invertebrate.

3. The transgenic organism of claim 1, wherein the organism is a fly.

4. The transgenic organism of claim 1, wherein the genome of the organism is homozygous for the mutant gene.

5. The transgenic organism of claim 1, wherein the organism is an insect.

6. The transgenic organism of claim 1, wherein the heterologous polynucleotide that is at least 99% identical to SEQ ID NO: 15 has been introduced into the organism's genome by homologous recombination.

7. The non-human transgenic organism of claim 1, wherein the polynucleotide is SEQ ID NO:15.

8. The transgenic organism of claim 7, wherein the organism is an invertebrate.

9. The transgenic organism of claim 7, wherein the organism is a fly.

10. The transgenic organism of claim 7, wherein the genome of the organism comprises two copies of the polynucleotide.

11. The transgenic organism of claim 7, wherein the heterologous polynucleotide of SEQ ID NO: 15 has been introduced into the organism's genome by homologous recombination.

12. A kit for use in screening compounds for activity, the kit comprising:
a non-human transgenic organism comprising a heterologous polynucleotide that is at least 99% identical to SEQ ID NO: 15 that encodes a receptor subunit and results in a reduced response of the transgenic organism to a spinosyn, relative to the parental organism that does not comprise the heterologous polynucleotide that is at least 99% identical to SEQ ID NO: 15.

13. A method for screening a compound, the method comprising:
i) providing a non-human transgenic organism comprising a heterologous polynucleotide that is at least 99% identical to SEQ ID NO: 15 that encodes a receptor subunit and results in a reduced response of the transgenic organism to a spinosyn, relative to the parental organism that does not comprise the heterologous polynucleotide that is at least 99% identical to SEQ ID NO: 15;
ii) administering the compound to said non-human transgenic organism of step (i); and
iii) observing the effect of the compound on said non-human transgenic organism of step (ii).

14. The method according to claim 13, wherein the transgenic organism is a vertebrate.

15. The method according to claim 13, wherein the transgenic organism is a fish.

16. The method according to claim 13, wherein the transgenic organism is a zebrafish.

17. The method according to claim 13, wherein the transgenic organism is a mouse.

* * * * *

```
                        SEQUENCE LISTING

<160> NUMBER OF SEQ ID NOS: 15

<210> SEQ ID NO 1
<211> LENGTH: 2424
<212> TYPE: DNA
<213> ORGANISM: Drosophila melanogaster

<400> SEQUENCE: 1
atgaaaaatg cacaactgaa actgactgaa gttgacgatg atgagctgtg gctggcagta      60
agattagcgc actgcagcag caactttagc agcagtagca gcacaagaac caccagcagc     120
aaccagaggc acaaccagca actcacaaca ctgcaaccaa ggagcttaag tacaaaacac     180
cacagcaaca ttgcaagcga gcagcacaat agccagcaac aggagccagc atcgaaggac     240
gaggatgtag ccaaccacgg tagaagcaat gaccagcaga cgcatctgca acagctagac     300
agcagcaaca tgttgtcgcc aaagacagcc gcagcagcaa ctgctgccgg cgatgaagca     360
acaacccaac aaccaacaaa cataagactg tgtgcacgca agcgacaacg attgcgtcgc     420
cgacgaaaaa gaaaaccagc aaccccaaac gaaacagata tcaagaaaca acagcaactt     480
agcatgcctc ccttcaaaac gcgcaaatcc acggacacct acagcacacc agcagcaaca     540
accagctgtc cgacagccac ctacatgcaa tgtcgagcca gcgacaatga gttcagtatt     600
ccgatatcga gacatgatag agtatccacg gccacattcg cctgggtgtt gcatgtgctg     660
caggtgctgc tcgtgtcgct gcaacagtgg caacttcacg tgcaacagcg atcggtgcta     720
ctgttcagaa ggatcgcagc gagcaccatc gccttcattt cctatttagg cagctttgca     780
gcgcaactga aaaatagcag cagcagcagt agcagcagca acagcagcaa caacagcagc     840
acgcaaatat taaacggact taataaacac tcatggatat ttttattgat atatttgaat     900
ttatctgcta aagtttgcct agcaggatat catgaaaaga gactgttaca cgatcttttg     960
gatccttata atacactaga acgtcccgtt ctcaatgaat cggacccgtt acaattaagc    1020
tttggtttaa ctttaatgca aattatcgat gtggacgaga aaaatcaatt gctagtcact    1080
aatgtgtggt aaaactgga gtggaacgac atgaatctcc gctggaacac ctccgactat    1140
ggcggagtta aggatctgcg aataccgccg catcgcatct ggaagccgga cgtgctgatg    1200
tacaacagtg cggatgaggg atttgacggc acctaccaga cgaacgtggt ggtgcggaac    1260
aacggctcgt gtctatacgt tccgccgggg atcttcaagt cgacgtgcaa gatcgacatc    1320
acgtggttcc ccttcgatga ccagcggtgc gagatgaagt tcggcagttg gacctacgac    1380
ggattccagc tggatttaca attacaagat gaaactggcg gtgatatcag cagttacgtg    1440
ctcaacggcg agtgggaact actgggtgtg cccggcaaac gtaacgagat ctattacaac    1500
tgctgcccgg aaccctatat agacatcacc ttcgccatca tcatccgccg acgaacactg    1560
tactatttct tcaacctgat catacccttgt gtactgattg cctccatggc cttgctcgga    1620
ttcaccctgc cgccagattc gggtgaaaaa ttatcgctgg gtgttaccat cttgctctcg    1680
ctgaccgtgt ttctgaatat ggttgccgag acaatgccgg ctacttccga tgcggtgcca    1740
ttgctgggta catatttcaa ttgcataatg tttatggtag cttcatccgt tgtgtcaacg    1800 atttttagtat taaattatca tcatcgaaat gctgatacgc acgaaatgtc cgaatggata    1860
cgcatcgtgt ttttgtgctg gctgccatgg atattgcgaa tgagtcgccc aggacgaccg    1920
```

```
ctgatcctag agtttccgac cacgccctgt tcggacacat cctccgagcg gaagcaccag    1980
atactctccg acgttgagct gaaagagcgc tcgtcgaaat cgctgctggc caacgtacta    2040
gacatcgatg atgacttccg gcacaattgt cgccccatga cgcccggcgg aacactgcca    2100
cacaacccgg ctttctatcg cacggtttat ggacaaggcg acgatggcag cattgggcca    2160
attggcagca cccgaatgcc ggatgcggtc acccatcata cgtgcatcaa atcatcaact    2220
gaatatgaat taggtttaat cttaaaggaa attcgcttta taactgatca gctacgtaaa    2280
gatgacgagt gcaatgacat tgccaatgat tggaaatttg cagctatggt cgttgacaga    2340
ctgtgcctta tcatattcac aatgttcgca atattagcca caatggctgt actactatca    2400
gcaccacata ttattgtctc gtag                                           2424

<210> SEQ ID NO 2
<211> LENGTH: 1616
<212> TYPE: DNA
<213> ORGANISM: Drosophila melanogaster

<400> SEQUENCE: 2
atgagcttcc cacaaccgca ctcattgccg gaggccactg caaacggtgg cagaatgctg      60
gtctatggcc tgggactttt aattatgata ccggcttgtg cggctggacc ccatgagaag     120
cggctactcc acgcccttct ggacaactac aacagcctgg agcgtccggt ggtcaatgaa     180
tccgatccat tgcaactgag cttcggacta acactcatgc agattatcga tgtggacgaa     240
aagaatcaac tgcttataac gaatatttgg ctcaaattgg aatggaacga tatgaatctt     300
cgatggaatt cgagtgagtt cggtggtgtg cgggatctgc gaattccgcc acatcgccta     360
tggaaaccgg atgtactgat gtacaacagt gccgacgagg gcttcgatgg aacgtacgcc     420
acaaatgtgg tggttcgcaa taatgggagc tgtctgtacg taccgccagg tatattcaag     480
tcaacgtgta aaatcgacat tacgtggttt ccattcgacg atcagagatg tgaaatgaaa     540
tttggttcgt ggacctacga tgggtttcag ttggacctgc agttgcagga cgaagctggt     600
ggcgacattt ctagctttat aaccaatggc gaatgggact tgttaggtgt gcccggtaaa     660
cgaaatgaaa tctactataa ttgctgccca gaaccttata ttgacataac attcgccatt     720
ttgataaggc gcaaaacgtt gtactatttt ttcaatctga ttgtgccgtg cgtactgatc     780
gcctccatgg cactgctagg gtttacactg ccaccagatt ctggtgaaaa gctttcgctt     840
ggagttacaa ttctattatc gcttacagtc ttcctcaaca tggtggccga acaatgccg     900 gcgacctccg atgcggtacc gctgctcgga acttatttca attgcattat gtttatggtg     960
gcctcatcag ttgtgtcaac catacttgtc ctcaattatc atcatagaaa tccagatacg    1020
catgaaatga gtgaatggat aagagtaata ttcctttatt ggttaccttg catattgcgc    1080
atgcaaagac ccggacaggt tggctacgaa tgtccgccgc cgccctcttc ttcgagttcc    1140
tccgcatccg gcgagaagaa gcaacagatc caaaacgttg agctaaagga gagatcctcc    1200
aagtctctgc tggccaatgt gctcgatata gacgatgatt tccgatgcaa tcatcgatgt    1260
gccagcgcga ctttgcccca ccagcccaca tattacagga cgatgtacag gcaagggat    1320 gacggcagcg tgggacccgt gggaccagct ggtccagttg tggacgggcg tttgcacgag    1380
gccatttccc acacctgtct gacatcctct gcggagtacg aactggcgct gatactcaag    1440
gagctgcgtt ggataacaga acagctcaaa aaagaggacg aaacaagcga cattacgcga    1500
gattggaaat ttgctgccat ggtcgtcgat cgtttgtgcc ttattatttt caccttgttt    1560
```

```
actattatag caaccctcgc tgtactcttc tcagcgccgc atttcatttt cccgta      1616

<210> SEQ ID NO 3
<211> LENGTH: 32
<212> TYPE: DNA
<213> ORGANISM: Drosophila melanogaster

<400> SEQUENCE: 3
ggatccatgg actccccgct gccagcgtcg ct                                 32

<210> SEQ ID NO 4
<211> LENGTH: 33
<212> TYPE: DNA
<213> ORGANISM: Drosophila melanogaster

<400> SEQUENCE: 4
ggatccttat tgcacgatta tgtgcggagc gga                                33

<210> SEQ ID NO 5
<211> LENGTH: 37
<212> TYPE: DNA
<213> ORGANISM: Drosophila melanogaster

<400> SEQUENCE: 5
tctagacacc atgaaaaatg cacaactgaa actgact                            37

<210> SEQ ID NO 6
<211> LENGTH: 33
<212> TYPE: DNA
<213> ORGANISM: Drosophila melanogaster

<400> SEQUENCE: 6
tctagactac gagacaataa tatgtggtgc tga                                33

<210> SEQ ID NO 7
<211> LENGTH: 34
<212> TYPE: DNA
<213> ORGANISM: Drosophila melanogaster

<400> SEQUENCE: 7
tctagacacc atgagcttcc cacaaccgca ctca                               34

<210> SEQ ID NO 8
<211> LENGTH: 33
<212> TYPE: DNA
<213> ORGANISM: Drosophila melanogaster

<400> SEQUENCE: 8
tctagattac gggaaaatga aatgcggcgc tga                                33

<210> SEQ ID NO 9
<211> LENGTH: 27
<212> TYPE: DNA
<213> ORGANISM: Caenorhabditis elegans

<400> SEQUENCE: 9
ggatccatgc aaaaactga acggcgt                                        27

<210> SEQ ID NO 10
<211> LENGTH: 30
<212> TYPE: DNA
<213> ORGANISM: Caenorhabditis elegans

<400> SEQUENCE: 10
```

```
ggatcctcaa gtctttttag gtctccgcct                                           30
```

<210> SEQ ID NO 11
<211> LENGTH: 14
<212> TYPE: PRT
<213> ORGANISM: Drosophila melanogaster

<400> SEQUENCE: 11

Ser Asn Arg Met Lys Glu Leu Glu Leu Lys Glu Arg Ser Ser
1               5                   10

<210> SEQ ID NO 12
<211> LENGTH: 34
<212> TYPE: DNA
<213> ORGANISM: Artificial Sequence
<220> FEATURE:
<223> OTHER INFORMATION: nucleotide sequence encoding a forward PCR
      primer for 30D nAChR alpha6 with an added Kozak translation
      initiation signal

<400> SEQUENCE: 12

```
actagtcacc atggactccc cgctgccagc gtcg                                      34
```

<210> SEQ ID NO 13
<211> LENGTH: 30
<212> TYPE: DNA
<213> ORGANISM: Artificial Sequence
<220> FEATURE:
<223> OTHER INFORMATION: nucleotide sequence encoding a reverse PCR
      primer for 30D nAChR alpha6.

<400> SEQUENCE: 13

```
actagtttat tgcacgatta tgtgcggagc                                           30
```

<210> SEQ ID NO 14
<211> LENGTH: 30
<212> TYPE: DNA
<213> ORGANISM: Artificial sequence
<220> FEATURE:
<223> OTHER INFORMATION: nucleotide sequence encoding a forward PCR
      primer for C. elegans ric3, with an added Kozak translation
      initiation signal

<400> SEQUENCE: 14

```
ggatccacca tgccaaaaac tgaacggcgt                                           30
```

<210> SEQ ID NO 15
<211> LENGTH: 1485
<212> TYPE: DNA
<213> ORGANISM: Drosophila melanogaster

<400> SEQUENCE: 15

```
atggactccc cgctgccagc gtcgctgtcg ctgtttgtcc tgttgatctt tctggcgata          60
attaaagaaa gctgtcaagg acctcatgaa aagcgcctgc tgaaccatct gctgtccacc         120
tacaatacgc tggagcgacc cgtggccaat gaatcggagc ccctggaggt taagttcgga         180
ctgacgctgc agcagatcat cgacgtggat gaaaagaatc agattctgac cacaaatgcg         240
tggttaaatt tggagtggaa cgactacaat ctgcgctgga tgaaacggaa atacggcggg         300
gtcaaggatt tacgaatcac gcccaacaag ctgtggaagc ccgacgtgct catgtacaac         360
agcgcggatg agggattcga tgcacgtat cacaccaaca ttgtggtcaa acataacggc         420
agttgtctgt acgtgccccc tggtatcttc aagagcacat gcaagataga catcacgtgg         480
```

```
ttcccatttg atgaccaaca ttgcgaaatg aaattcggta gttggactta cgatggaaat    540
cagttggatt tggttttgaa ttccgaagat ggagggatc tttccgattt cataacaaat     600
ggcgagtggt acttgcttgc catgccggga aagaagaata cgatagtcta cgcctgctgc    660
ccagaaccat atgtcgatat caccttact atacagattc gtcgccgtac attatattat     720
tttttcaatt taatcgtgcc atgtgtgcta atctcatcga tggccctact gggcttcaca    780
ttgccgccgg attcgggcga gaaactgacg ctgggcgtaa ctatactact atcattaaca    840
gtatttctaa accttgtcgc cgagtccatg ccgacaacgt cggatgctgt tcctcttata    900
ggcacctact tcaattgcat catgttcatg gtcgcatcgt cggtggtgct gacagtagtg    960
gtgctcaact accaccatcg cacagcggac attcacgaga tgccaccgtg gatcaagtcc   1020
gttttcctac aatggctgcc ctggatcttg cgaatgggtc gacccggtcg caagattaca   1080
cgcaaaacaa tactattaag caatcgcatg aaggagctgg agctaaagga gcgctcctcc   1140
aaatccctgc tggccaatgt cctcgacatc gacgacgact ttcggcacac aatatctggc   1200
tcccaaaccg ccattggctc gtcggccagc ttcggtcggc ccacaacggt ggaggagcat   1260
cacacggcca tcggctgcaa tcacaaagat cttcatctaa ttcttaaaga attgcaattt   1320 attacgcgc ggatgcgcaa agctgacgac gaagcggaat tgatcggcga ttggaagttc    1380
gcggcaatgg ttgtggatag attttgttta attgttttca cgctcttcac gattattgca   1440
acggttacgg tgctgctctc cgctccgcac ataatcgtgc aataa                   1485
```